(12) United States Patent
Urabe et al.

(10) Patent No.: US 12,082,976 B2
(45) Date of Patent: Sep. 10, 2024

(54) ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

(71) Applicant: Konica Minolta, Inc., Tokyo (JP)

(72) Inventors: Makiko Urabe, Kanagawa (JP); Akihiro Kawabata, Tokyo (JP); Yoshihiro Takeda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/514,326

(22) Filed: Oct. 29, 2021

(65) Prior Publication Data

US 2022/0133280 A1 May 5, 2022

(30) Foreign Application Priority Data

Nov. 4, 2020 (JP) ................................ 2020-184389

(51) Int. Cl.
*A61B 8/00* (2006.01)
*A61B 8/06* (2006.01)
*A61B 8/14* (2006.01)

(52) U.S. Cl.
CPC .................. *A61B 8/54* (2013.01); *A61B 8/06* (2013.01); *A61B 8/14* (2013.01); *A61B 8/463* (2013.01)

(58) Field of Classification Search
CPC .... A61B 8/54; A61B 8/06; A61B 8/14; A61B 8/463; A61B 8/5223; A61B 8/0891; A61B 8/488; A61B 8/52
See application file for complete search history.

(56) References Cited

U.S. PATENT DOCUMENTS

2001/0016686 A1\* 8/2001 Okada .................. A61B 8/0858
600/454
2003/0060710 A1\* 3/2003 Salgo .................. G01S 7/52085
600/443
(Continued)

FOREIGN PATENT DOCUMENTS

JP 2011-010789 A 1/2011
JP 2014-207979 A 11/2014
(Continued)

OTHER PUBLICATIONS

Office Action dated May 18, 2023 for corresponding Chinese Patent Application No. 202111299160.7, with English translation.
(Continued)

*Primary Examiner* — Adil Partap S Virk
(74) *Attorney, Agent, or Firm* — Lucas & Mercanti, LLP

(57) ABSTRACT

Provided is an ultrasound diagnostic apparatus for generating a tomographic image of a subject by transmitting and receiving an ultrasound, the ultrasound diagnostic apparatus including: a hardware processor that: detects a blood vessel imaged in the tomographic image; determines whether an image of the blood vessel which has been detected falls under either a short axis view or a long axis view by an image analysis of the tomographic image; and sets a steering angle of an ultrasound beam used in measuring conditions of the detected blood vessel or a blood flow velocity in the detected blood vessel, based on a determination result of the image of the blood vessel.

16 Claims, 20 Drawing Sheets

(56) References Cited

U.S. PATENT DOCUMENTS

| | | | |
|---|---|---|---|
| 2003/0149366 A1* | 8/2003 | Stringer | A61B 8/42 600/464 |
| 2007/0055149 A1* | 3/2007 | Suzuki | A61B 5/02007 600/437 |
| 2007/0060818 A1* | 3/2007 | Likubo | A61B 5/1075 600/437 |
| 2008/0009737 A1* | 1/2008 | Takimoto | A61B 8/06 600/443 |
| 2009/0030320 A1* | 1/2009 | Ishihara | A61B 8/06 600/454 |
| 2010/0210946 A1* | 8/2010 | Harada | A61B 8/4281 600/443 |
| 2010/0268084 A1* | 10/2010 | Osaka | A61B 8/463 600/443 |
| 2012/0059264 A1* | 3/2012 | Hope Simpson | A61B 8/488 600/454 |
| 2012/0108971 A1* | 5/2012 | Miyama | A61B 8/06 600/443 |
| 2012/0116227 A1* | 5/2012 | Suzuki | G01S 7/52073 600/443 |
| 2012/0136256 A1* | 5/2012 | Nozaki | A61B 8/469 600/459 |
| 2012/0296214 A1* | 11/2012 | Urabe | A61B 8/4444 600/447 |
| 2014/0276072 A1* | 9/2014 | Martins | A61B 8/463 600/454 |
| 2014/0324475 A1* | 10/2014 | Ochi | G16H 30/40 705/3 |
| 2014/0371593 A1* | 12/2014 | Kondoh | A61B 8/0858 600/443 |
| 2015/0272541 A1* | 10/2015 | Hyuga | G16H 50/30 600/443 |
| 2016/0000408 A1* | 1/2016 | Matsunaga | A61B 8/463 600/443 |
| 2016/0270757 A1* | 9/2016 | Toma | A61B 8/5223 |
| 2016/0302761 A1* | 10/2016 | Lee | G16H 50/30 |
| 2017/0164923 A1* | 6/2017 | Matsumoto | A61B 5/026 |
| 2019/0343482 A1* | 11/2019 | Abe | A61B 8/0883 |
| 2020/0174119 A1* | 6/2020 | Tadross | A61B 8/5223 |
| 2022/0031288 A1* | 2/2022 | Yamamoto | A61B 8/463 |
| 2022/0061810 A1* | 3/2022 | Dickie | A61B 8/463 |
| 2022/0370034 A1* | 11/2022 | Chen | A61B 8/0841 |
| 2022/0378394 A1* | 12/2022 | Yamamoto | A61B 8/488 |
| 2023/0127935 A1* | 4/2023 | Chen | A61B 8/5238 382/131 |
| 2023/0143880 A1* | 5/2023 | Jago | A61B 8/06 600/454 |

FOREIGN PATENT DOCUMENTS

| | | |
|---|---|---|
| JP | 2014-213030 A | 11/2014 |
| JP | 2017-108769 A | 6/2017 |

OTHER PUBLICATIONS

Office Action dated Oct. 24, 2023 for corresponding Chinese Patent Application No. 202111299160.7, with English translation.

Chinese Patent Office, "Rejection Decision" dated Jan. 24, 2024, which was issued for the corresponding Chinese Patent Application No. 202111299160.7, with English translation, 20 pages.

Japanese Patent Office, Notice of Reasons for Refusal mailed Jul. 30, 2024, which was issued for related Japanese Patent Application No. 2020-184389, with English translation, 9 pages.

* cited by examiner

ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

CROSS REFERENCE TO RELATED APPLICATIONS

The entire disclosure of Japanese Patent Application No. 2020-184389 filed on Nov. 4, 2020 is incorporated herein by reference in its entirety.

BACKGROUND

Technological Field

The present disclosure relates to an ultrasound diagnostic apparatus, a method of controlling an ultrasound diagnostic apparatus, and a non-transitory computer-readable recording medium storing therein a computer-readable program for controlling an ultrasound diagnostic apparatus.

Description of Related Art

An ultrasound diagnostic apparatus is known which transmits ultrasound toward a subject, receives waves reflected by the subject and performs predetermined signal processing on the reception signal to visualize a shape, conditions or a behavior of the inside of the subject in the form of a tomographic image. An ultrasound diagnostic apparatus can obtain a tomographic image with a simple operation of applying an ultrasound probe to a body surface or inserting the ultrasound probe into the body and thus is safe and puts a smaller burden on the subject.

Conventionally, in this type of ultrasound diagnostic apparatus, functions are implemented such as a color Doppler mode, a power Doppler mode, and a PW Doppler mode that measure a blood flow velocity in the subject by a Doppler shift frequency of an ultrasound echo when an ultrasound beam is transmitted.

In the color Doppler mode, power Doppler mode, or PW Doppler mode, a user sets a sample gate position and/or a region of interest (hereinafter referred to as a "ROI") on a tomographic image of the subject. Then, in such color Doppler mode, power Doppler mode or PW Doppler mode, ultrasound echo from the sample gate position or ROIs of the subject is selectively extracted, and thereby the ultrasound echo from the blood flow in the subject and the Doppler shift frequency of transmission frequencies is detected. The blood flow velocity is thus converted from the Doppler shift frequency, considering an angle correction value corresponding to a crossing angle between a beam direction of an ultrasound beam and a blood flow direction (hereinafter, abbreviated as an "angle correction value"), and using, for example, the following Expression 1.

$$V = c2 \cos\theta \times FD/F0 \qquad \text{Expression 1}$$

(where, V: bloodflow velocity, F0: transmission frequency (or reception frequency) of ultrasound beam, Fd: Doppler shift frequency, c: sound velocity in living body, and θ: angle correction value)

Generally, for the purpose of improving detection accuracy of the Doppler shift frequency, this type of ultrasound diagnostic apparatus performs, prior to execution of the Doppler mode, processing for changing a direction of a steering angle of the ultrasound beam (i.e., angle of beam direction of ultrasound beam with respect to tomographic image depth direction; hereinafter the same) from zero angle (i.e., tomographic image depth direction) to the angle along an extending direction of a blood vessel (i.e., blood flow direction) so as to reduce as much as possible the crossing angle between the beam direction of the ultrasound beam and the blood flow direction (e.g., see Japanese Patent Application Laid Open No. 2011-010789 (hereinafter, Patent Literature (PTL) 1)).

Note that, this type of ultrasound diagnostic apparatus requires to reduce an operation load for a user as much as possible so that ultrasonography can be performed even by an unskilled user.

From this point of view, for example, PTL 1 describes a method for automatically setting a steering angle such that color Doppler images are obtained respectively in different directions of a sound ray (0°, +30°, −30°), and then the sound ray is directed in the direction (+30°) from which the color Doppler image with the highest image quality is obtained among the directions.

However, a blood vessel imaged in a tomographic image is not necessarily a long axis view (indicating a blood vessel image in which a longitudinal cross section or a blood vessel is imaged; hereinafter the same), as assumed in PTL 1, and a case of a short axis view (indicating a blood vessel image in which a lateral cross section of a blood vessel is imaged; hereinafter the same) is also included.

FIG. 1A illustrates an example of a short axis view of a blood vessel, and FIG. 1B illustrates an example of a long axis view of a blood vessel. Incidentally, in FIGS. 1A and 1B, regions surrounded by dotted lines are the regions of the blood vessel.

In this regard, the related art described in PTL is configured to set a steering angle without changing processing depending on whether an image of a blood vessel imaged in a tomographic image is a short axis view or a long axis view. However, in a case where the image of the blood vessel imaged in the tomographic image is the short axis view, the related art described in PTL may set an inappropriate sleeting angle because changing the sleeting angle does not cause a large difference in the image quality of the color Doppler image. In addition, the related art described in PTL 1 requires to generate a plurality of two-dimensional blood flow images in different directions of a sound ray by changing the direction of a sound ray so as to set the steering angle; thus, a problem arises in that it takes time for setting.

Note that, in recent ultrasonography, both the short axis view and long axis view of a blood vessel may be imaged for the purpose of, for example, observing a narrowing of a carotid artery. In such ultrasonography, for example, in order to check the presence or absence of a narrowing, a short axis view of a blood vessel is extracted in a B-mode image, and a ROI in a color Doppler mode is set on a target blood vessel to extract blood flow information in a color Doppler mode, and after the checking, a user changes an angle of an ultrasound probe to extract a narrowing portion in a long axis view or the blood vessel and thereby observes the amount or blood flow and measures a diameter in the vicinity of the narrowing portion. In such a case, in the related art according to PTL 1, a steering angle is set to an inappropriate angle each time a blood vessel changes to a short axis view, which possibly causes the user to manually reset the angle every time.

SUMMARY

The present disclosure has been made in view of the above-described problems, and an object thereof is to provide an ultrasound diagnostic apparatus, a method of controlling an ultrasound diagnostic apparatus, and a non-transitory computer-readable recording medium storing therein a computer-readable program for controlling an ultrasound diagnostic apparatus, which are capable of reducing an operation load for a user when executing a Doppler mode, and of performing measurement of a blood flow state with high reliability.

To achieve at least one of the abovementioned objects, according to an aspect of the present invention, an ultrasound diagnostic apparatus reflecting one aspect of the present invention is an apparatus for generating a tomographic image of a subject by transmitting and receiving an ultrasound, the ultrasound diagnostic apparatus including:
a hardware processor that:
detects a blood vessel imaged in the tomographic image;
determines whether an image of the blood vessel which has been detected falls under either a short axis view or a long axis view by an image analysis of the tomographic image; and
sets a steering angle of an ultrasound beam used in measuring conditions of the detected blood vessel or a blood flow velocity in the detected blood vessel, based on a determination result of the image of the blood vessel.

To achieve at least one of the abovementioned objects, according to an aspect of the present invention, a method reflecting one aspect of the present invention is a method of controlling an ultrasound diagnostic apparatus for generating a tomographic image of a subject by transmitting and receiving an ultrasound, the method including:
detecting a blood vessel imaged in the tomographic image;
determining whether an image of the blood vessel which has been detected falls under either a short axis view or a long axis view by an image analysis of the tomographic image; and
setting a steering angle of an ultrasound beam used in measuring conditions of the detected blood vessel or a blood flow velocity in the detected blood vessel, based on a determination result of the determining.

To achieve at least one of the abovementioned objects, according to an aspect of the present invention, a non-transitory computer-readable recording medium reflecting one aspect of the present invention is a medium storing therein a computer-readable program for controlling an ultrasound diagnostic apparatus for generating a tomographic image of a subject by transmitting and receiving an ultrasound, the program causing a computer to perform processing including:
detecting a blood vessel imaged in the tomographic image;
determining whether an image of the blood vessel which has been detected falls under either a short axis view or a long axis view by an image analysis of the tomographic image; and
setting a steering angle of an ultrasound beam used in measuring conditions of the detected blood vessel or a blood flow velocity in the detected blood vessel, based on a determination result of the determining.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1A:
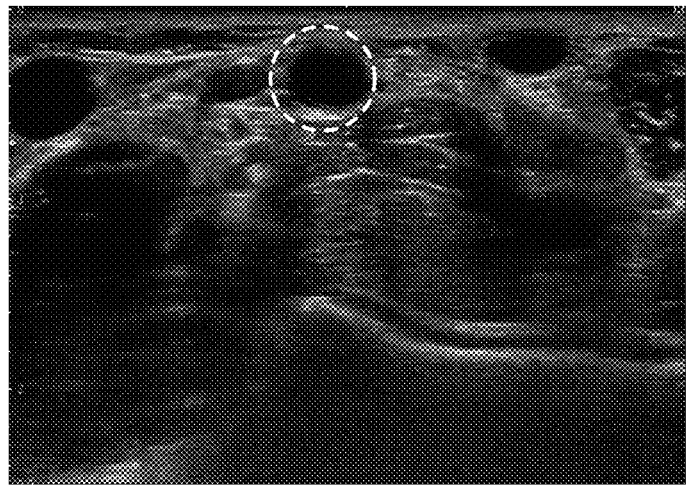
FIG. 1A illustrates an example of a short axis view of a blood vessel.
Figure 1B:
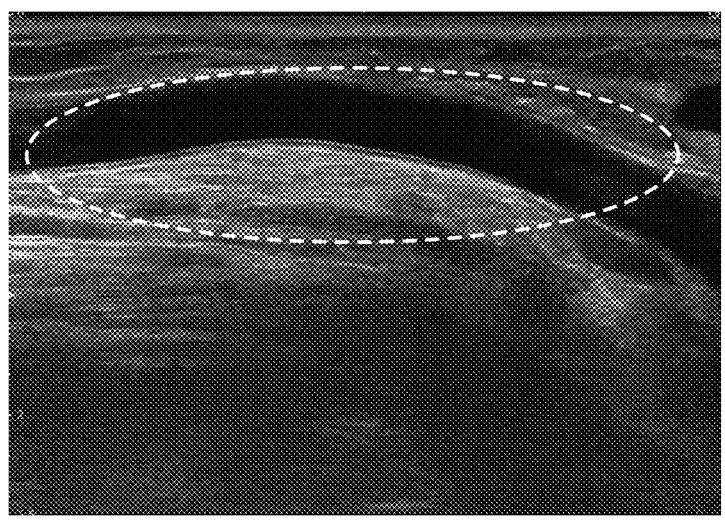
FIG. 1B illustrates an example of a long axis view of a blood vessel.

Hereinafter, one or more embodiments of the present invention will be described with reference to the drawings. However, the scope of the invention is not limited to the disclosed embodiments.

Hereinafter, preferred embodiments of the present disclosure will be described in detail with reference to the attached drawings. Note that, components having substantially the same functions are assigned the same reference numerals in the description and drawings to omit duplicated descriptions thereof.

Configuration of Ultrasound Diagnostic Apparatus

Hereinafter, a configuration of an ultrasound diagnostic apparatus according to an embodiment of the present invention will be described with reference to FIGS. 2 to 4.

Figure 2:
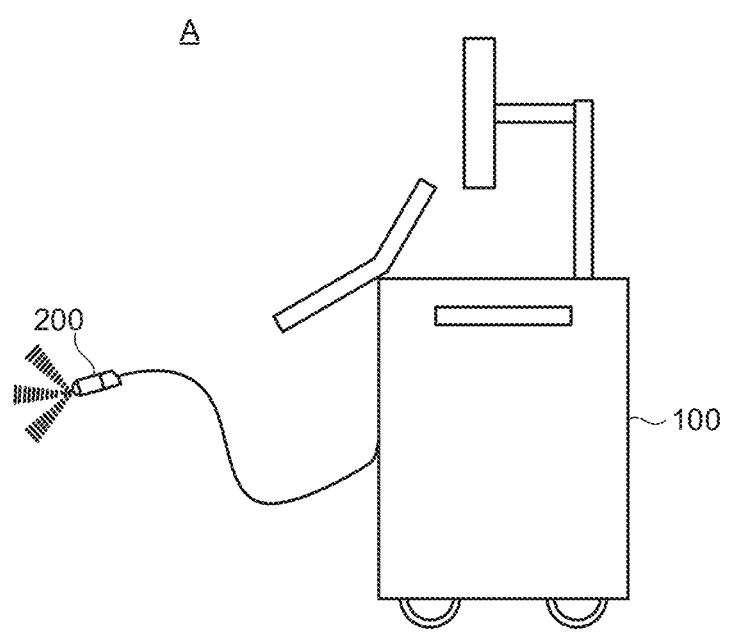
FIG. 2 illustrates an example of an external view of an ultrasound diagnostic apparatus.
Figure 3:
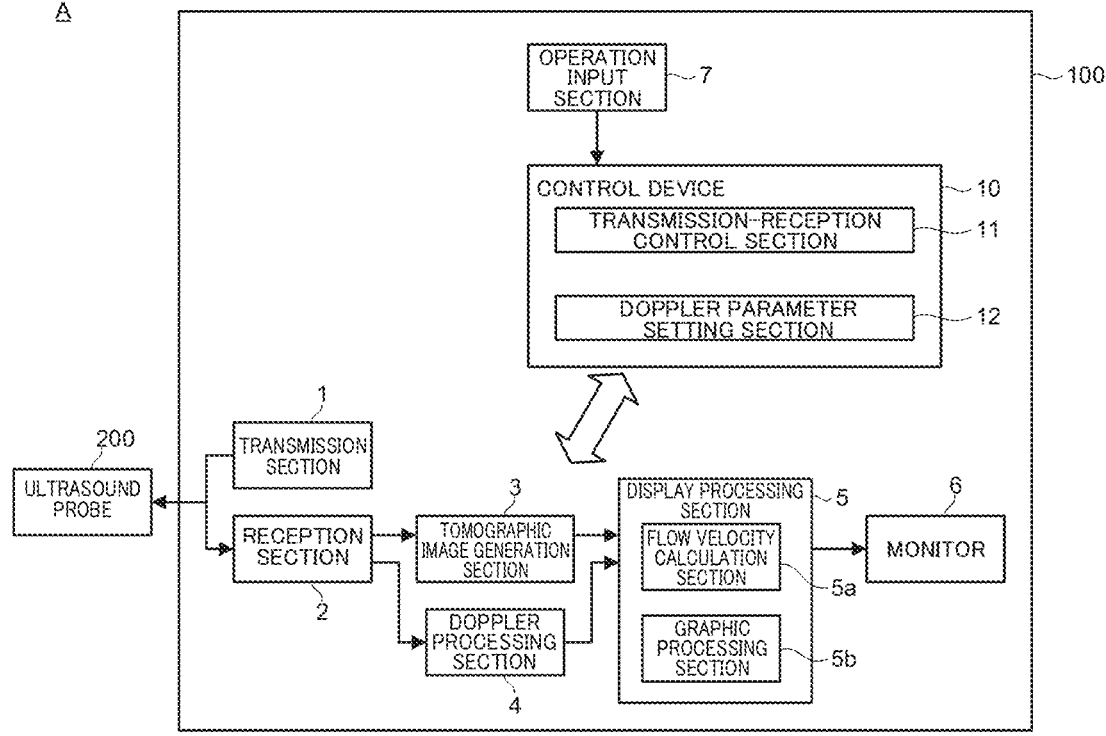
FIG. 3 illustrates an example of an overall configuration of the ultrasound diagnostic apparatus.

FIG. 2 illustrates an example of an external view of ultrasound diagnostic apparatus A. FIG. 3 illustrates an example of an overall configuration of ultrasound diagnostic apparatus A.

Figure 4:
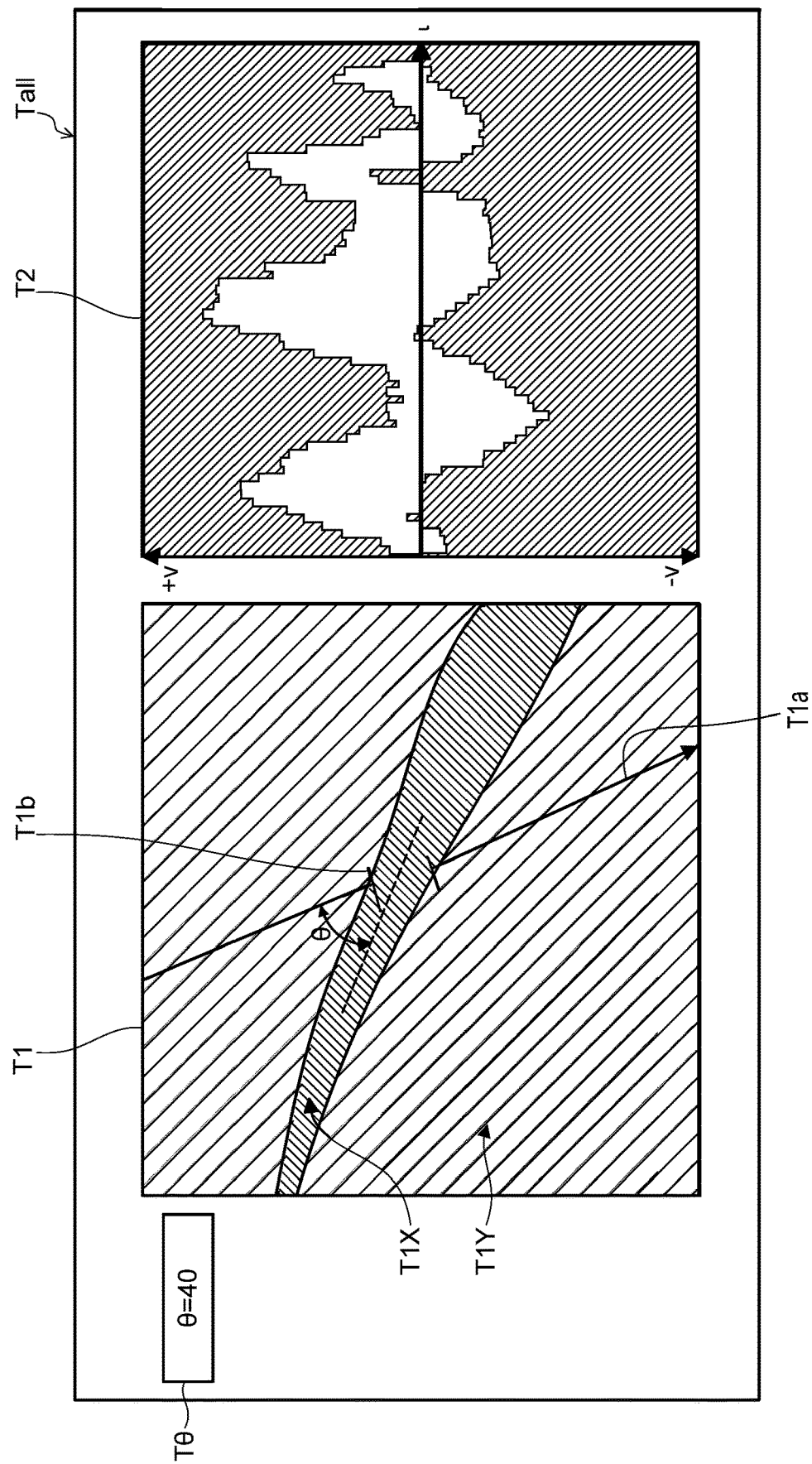
FIG. 4 illustrates an example of a monitor screen which is displayed at the time of measuring a blood flow in the ultrasound diagnostic apparatus.

FIG. 4 illustrates an example of a monitor screen which is displayed at the time of measuring a blood flow in ultrasound diagnostic apparatus A.

Ultrasound diagnostic apparatus A is used to visualize the shape, conditions or behavior of an inside of a subject as an ultrasound image to perform an image diagnosis. Note that, in the present embodiment, a description will be given of an aspect in which ultrasound diagnostic apparatus A executes a B-mode operation and a PW Doppler-mode operation in time division to generate a tomographic image and a Doppler spectrum image (see FIG. 4). However, ultrasound diagnostic apparatus A of the present invention may be applied to an apparatus in which a color Doppler mode or a power Doppler mode are implemented in addition to or instead of the PW Doppler mode.

As illustrated in FIG. 2, ultrasound diagnostic apparatus A includes ultrasound diagnostic apparatus main body 100 and ultrasound probe 200.

Ultrasound probe 200 functions as an acoustic sensor that transmits an ultrasound beam (here, approximately 1 to 30 MHz) into a subject (for example, a human body), receives an ultrasound echo resulting from part of the transmitted ultrasound beam reflected in the subject, and converts the ultrasound echo alto an electric signal.

A user brings an ultrasound-beam transmission-reception surface of ultrasound probe 200 into contact with a subject, operates ultrasound diagnostic apparatus A, and performs an ultrasound diagnosis. Note that, it is assumed here that ultrasound probe 200 transmits an ultrasound beam from an outer surface of the subject into the subject and receives the resulting ultrasound echo. However, ultrasound probe 200 may be an ultrasound probe that is used by being inserted into e.g. the alimentary canal or a blood vessel, or into the coelom or the like. Further, as ultrasound probe 200, any probe such as a convex probe, a linear probe, a sector probe, or a 3D probe is applicable.

Ultrasound probe 200 is configured to include, for example, a plurality of transducers (e.g., piezoelectric elements) arranged in a matrix and a channel switching section (e.g., a multiplexer) for executing switching control to turn on and off of the driving states of the plurality of transducers individually or for each block thereinafter referred to as "channel").

Each transducer of ultrasound probe 200 converts a voltage pulse generated by ultrasound diagnostic apparatus main body 100 (transmission section 1) into an ultrasound beam, transmits the ultrasound beam into a subject, receives an ultrasound echo reflected in the subject, converts the ultrasound echo into an electric signal (hereinafter referred to as "reception signal"), and outputs the reception signal to ultrasound diagnostic apparatus main body 100 (reception section 2).

Ultrasound diagnostic apparatus main body 100 includes transmission section 1, reception section 2, tomographic image generation section 3, Doppler processing section 4, display processing section 5, monitor 6, operation input section 7, and control device 10.

Transmission section 1 is a transmitter that sends out a voltage pulse that is a driving signal to ultrasound probe 200. Transmission section 1 is configured to include, for example, a high-frequency pulse oscillator, and a pulse setting section (neither is illustrated). Transmission section 1 adjusts a voltage pulse generated by the high-frequency pulse oscillator to a voltage amplitude, a pulse width, and a sending-out timing set by the pulse setting section, and sends out the voltage pulse for each channel of ultrasound probe 200.

Transmission section 1 includes the pulse setting section for each of a plurality of channels of ultrasound probe 200 and is configured such that the voltage amplitude, the pulse width, and the sending-out timing of the voltage pulse can be set for each of the plurality of channels. For example, transmission section sets appropriate delay times for the plurality of channels to change a target depth or generate different pulse waveforms (for example, transmission section 1 sends out a single-wave pulse in the B-mode and a four-wave pulse in the PW Doppler mode).

Reception section 2 is a receiver that performs a reception process of a reception signal related to an ultrasound echo and generated by ultrasound probe 200. Reception section 2 is configured to include a preamplifier, an AD conversion section, a reception beamformer, and a processing system switching section (none of them is illustrated).

The preamplifier of reception section 2 amplifies a reception signal related to a weak ultrasound echo for each channel, and the AD conversion section of reception section 2 converts the reception signal into a digital signal. In addition, the reception beamformer of reception section 2 unifies reception signals of the plurality of channels by phasing addition of reception signals of the respective channels, to thereby generate acoustic line data. Further, the processing system switching section of reception section 2 controls switching between sections to which the reception signal generated by the reception beamformer is transmitted, and outputs the reception signal to one of tomographic image generation section 3 or Doppler processing section 4 in accordance with the operation mode to be executed.

Tomographic image generation section 3 acquires a reception signal from reception section 2 when in the B-mode operation, and generates a tomographic image (also referred to as "B-mode image") of the inside of the subject.

For example, tomographic image generation section 3 temporally continuously accumulates, in a line memory, signal intensities of an ultrasound echo detected after ultrasound probe 200 transmits a pulsed ultrasound beam in the depth direction. In addition, along with scanning of the inside of the subject by using the ultrasound beam from ultrasound probe 200, tomographic image generation section 3 successively accumulates the signal intensities of the ultrasound echo at scanning positions in the line memory, to thereby generate two-dimensional data used as a frame unit. Further, tomographic image generation section 3 generates a tomographic image by converting the signal intensities of the ultrasound echo detected at the positions of the inside of the subject into a luminance value.

Tomographic image generation section 3 is configured to include, for example, an envelope detection circuit, a dynamic filter and a logarithmic compression circuit. The envelope detection circuit performs envelope detection on the reception signal to detect signal intensity. The logarithmic compression circuit performs logarithmic compression on the signal intensity of the reception signal detected by the envelope detection circuit. The dynamic filter is a band-pass filter whose frequency characteristic is changed according to the depth, and removes a noise component included in the reception signal.

Doppler processing section 4 acquires the reception signal from reception section 2 when in a PW Doppler mode operation, color Doppler mode operation, or power Doppler mode operation to detect a Doppler shift frequency with respect to a transmission frequency of the ultrasound echo from the blood flow.

For example, Doppler processing section 4, in the PW Doppler mode operation, samples the reception signal related to the ultrasound echo in synchronization with a pulse repetition frequency while ultrasound probe 200 transmits pulsed ultrasound beams at regular intervals according to the pulse repetition frequency. Then, Doppler processing section 4 detects the Doppler shift frequency based on, for example, a phase difference between the ultrasound echo according to the nth ultrasound beam and the ultrasound echo related to the n+1-th ultrasound beam, which are from the same sample gate position.

Doppler processing section 4 is configured to include, for example, a quadrature detection section, a low-pass filter, a range gate, and an FFT-analysis section (none of them is illustrated). The quadrature detection section mixes, with respect to the reception signal, a reference signal in phase with the transmitted ultrasound beam and a reference signal in different phase with the transmitted ultrasound beam by $\pi/2$ to generate a quadrature detection signal. The low-pass filter removes a high frequency component of the quadrature detection signal to generate a reception signal related to the Doppler shift frequency. The range gate acquires only an ultrasound echo from the sample gate position. The FFT analysis section calculates the Doppler shift frequency of the ultrasound echo based on a temporal variation of the reception signal output from the range gate.

Display processing section 5 obtains the tomographic image output from tomographic image generation section 3 and the Doppler shift frequency of the ultrasound echo output from Doppler processing section 4 to thereby generate an image for display (hereinafter may be referred to as a "display image") to be displayed on monitor 6 (see FIG. 4).

Display processing section 5 includes flow velocity calculation section 5a and graphic processing section 5b.

Flow velocity calculation section 5a calculates a blood flow velocity in the sample gate position or ROI when in the PW Doppler mode operation, color Doppler mode operation, or power Doppler mode operation Flow velocity calculation section 5a, for example, using the above-described Equation 1, calculates the blood flow velocity front the Doppler shift frequency of the ultrasound echo output front Doppler processing section 4. Correction value θ at this time (correction value corresponding to crossing angle between beam direction of ultrasound beam and extending direction of blood vessel) is set, by a command from control device 10 (Doppler parameter setting section 12).

Flow velocity calculation section 5a, when in the PW Doppler mode operation, for example, as illustrated in FIG. 4, generates a Doppler spectrum image (T2 in FIG. 4) indicating a time-series distribution of the blood flow velocities. The Doppler spectrum image is an image in which the time is represented by the horizontal axis and the blood flow velocity is represented by the vertical axis. In the Doppler spectrum image, for example, the blood flow velocity at each time point is represented in a single line-like form, and power of each blood flow velocity (that is, each frequency) is represented by a magnitude of luminance of a pixel (illustration of changes luminance is omitted in FIG. 4). Incidentally, flow velocity calculation section 5a, when in the color Doppler mode operation or power-Doppler mode operation, generates a color Doppler image obtained by imaging the blood flow velocity at each position of the ROI (not illustrated).

Graphic processing section 5b performs a predetermined image process such as a coordinates transformation process and a data interpolation process on the tomographic image output from tomographic image generation section 3. Then, graphic processing section 5b combines the tomographic image subjected to the image process and the Doppler spectrum image to thereby generate the display image.

In addition, graphic processing section 5b obtains information related to the sample gate position, the sample gate size, the steering angle of the ultrasound beam, and angle correction value which are set in control device 10 (here, Doppler parameter setting section 12), and embeds images corresponding to the information (e.g., these numerical values and marks) in the display image so that the user can recognize the information. Incidentally, graphic processing section 5b, for example, displays the images indicating the sample gate position, the sample gate size, the steering angle of the ultrasound beam, and a direction of blood flow (extending direction of blood vessel) so as to superimpose the images on the tomographic image.

The monitor screen of FIG. 4 is a display image generated by graphic processing section Sb when the B-mode operation and PW Doppler mode operation are executed in parallel. Tall in FIG. 4 denotes an entire region of the display image, T1 denotes a tomographic image (T1X denotes blood flow region, T1Y denotes tissue region), T1a denotes the steering angle of the ultrasound beam during the PW Doppler mode operation, T1b denotes the sample gate position of the ultrasound beam during the PW Doppler mode operation, T2 denotes the Doppler spectrum image, and T$\theta$ denotes an angle-correction-value display box indicating the angle correction value.

Note that, tomographic image generation section 3, Doppler processing section 4, and display processing section 5 are implemented as, for example, a digital operation circuit formed by a digital signal processor (DSP) or the like. However, these configurations can be modified in various manners and, for example, some or all thereof may be implemented as a dedicated hardware circuit or may be implemented by operation processing in accordance with a program.

Monitor 6 is a display that displays a display image generated by display processing section 5, and is, for example, configured as a liquid crystal display.

Operation input section 7 is a user interface for a user to perform an input operation and is formed by, for example, a mouse, a push-button switch, a keyboard, and/or the like. Operation input section 7 converts an input operation performed by a user into an operation signal and inputs the operation signal into control device 10.

Control device 10 transmits and receives signals to and from ultrasound probe 200, transmission section 1, reception section 2, tomographic image generation section 3, Doppler processing section 4, display processing section 5, monitor 6, and operation input section 7, and integrally controls these sections. Note that, control device 10 includes, for example, a central processing unit (CPU), a read-only memory (ROM), a random access memory (RAM), and the like. In addition, each function of control device 10 is implemented by the CPU referring to a control program and various types of data stored in the ROM or the RAM. However, some or all of the functions of control device 10 are not necessarily implemented by processing by software, and can of course also be implemented by a dedicated hardware circuit or a combination thereof.

Control device 10 includes transmission-reception control section 11 and Doppler parameter setting section 12.

Transmission-reception control section. 11 controls the channel switching section (not illustrated) of ultrasound probe 200 to selectively determine driving target channels among the plurality of channels. Further, transmission-reception control section 11 controls each of transmission section 1 and reception section 2 to transmit and receive ultrasound for the driving target channels.

When in the B-mode operation (i.e., in generating a tomographic image), transmission-reception control section 11 sequentially drives the driving target channels among the plurality of channels along the scanning direction, thereby causing ultrasound probe 200 to scan the inside of the subject with ultrasound.

When in the PW Doppler mode operation, color Doppler mode operation, or power Doppler mode operation (i.e., in measuring the blood now velocity), transmission-reception control section 11 selectively drives the plurality of transducers provided in ultrasound probe 200 such that an ultrasound beam is transmitted from ultrasound probe 200 towards a sample gate position or a ROI in the subject at a predetermined angle. In addition, transmission-reception control section 11 controls transmission section 1 such that pulsed ultrasound beams (burst waves) are repeatedly transmitted at a predetermined pulse repetition frequency from ultrasound probe 200, and controls reception section 2 such that controls reception section 2 receives ultrasound echoes of the ultrasound beams.

Transmission-reception control section 11 basically determines transmission and reception conditions of an ultrasound beam based on, for example, the type of ultrasound probe 200 (e.g., convex type, sector type, linear type or the like), the depth of an imaging target in the subject, and the imaging mode (e.g., B-mode, PW Doppler mode, color Doppler mode, or power Doppler mode), which are set by a user via operation input section 7.

When in the PW Doppler mode operation, however, transmission-reception control section 11 determines the transmission and reception conditions of an ultrasound beam based on a sample gate position, the size of the sample gate position, and a steering angle of the ultrasound beam, which are set by Doppler parameter setting section 12. Note that, transmission-reception control section 11 obtains the sample gate position, the size of the sample gate position, and a steering angle of the ultrasound beam, which are set by Doppler parameter setting section 12 by, for example, appropriately setting the number of a channel of a driving target to be used in the PW Doppler mode, the delay time in each channel, or the like.

Doppler parameter setting section 12 sets various parameters so as to accurately detect the velocity of blood flow through blood vessels in the subject when in the PW Doppler mode operation, color Doppler mode operation, or power Doppler mode operation (in the present embodiment, PW Doppler mode operation). Doppler parameter setting section 12 automatically sets the sample gate position, the size of the sample gate position, and the steering angle of the ultrasound beam, based on image information on a tomographic image.

However, Doppler parameter setting section 12 may have a function to automatically set the sample gate position, the size of the sample gate position, and the steering angle of the ultrasound beam as well as a function to manually set them by an operation of the user.

Detailed Configuration of Doppler Parameter Setting Section 12

Next, a detailed configuration of Doppler parameter setting section 12 will be described with reference to FIGS. 5 to 10. Here, a description will be given of setting processing of a measurement region or the like of Doppler parameter setting section 12 in executing the PW Doppler mode, but Doppler parameter setting section 12 may perform, using the same processing, setting processing of a ROI in the color Doppler mode and the power Doppler mode and setting processing of a steering angle.

Figure 5:
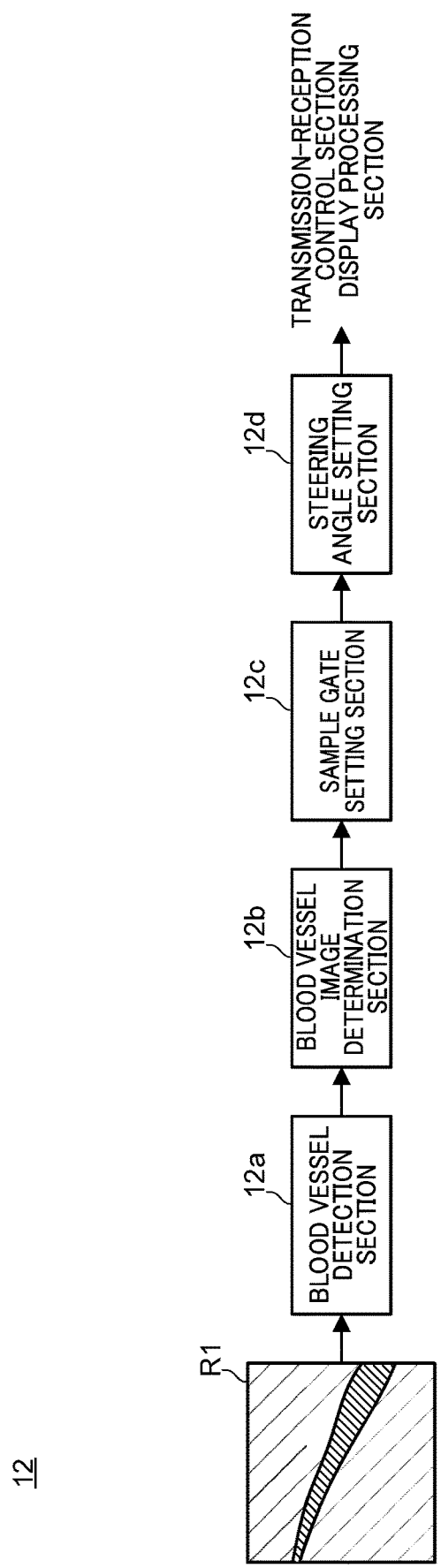
FIG. 5 illustrates an example of a detailed configuration of a Doppler parameter setting section.

FIG. 5 illustrates an example of a detailed configuration of Doppler parameter setting section 12.

Doppler parameter setting section 12 includes blood vessel detection section 12a, blood vessel image determination section 12b, sample gate setting section 12c, and steering angle setting section 12d.

Blood Vessel Detection Section 12a

Blood vessel detection section 12a obtains tomographic image R1 generated by tomographic image generation section 3 and detects the blood vessel imaged in tomographic image R1, based on image information on tomographic image R1. Blood vessel detection section 12a uses data of a blood vessel pattern recorded in a memory (not illustrated) in advance (hereinafter, also referred to as a "blood vessel template image") to thereby detect the blood vessel imaged in tomographic image R1 by using, for example, publicly known template matching.

Then, blood vessel detection section 12a sets, for example, a region where the blood vessel imaged most clearly in tomographic image R1 as a sample gate position of a target of a Doppler process (i.e., a center position of the sample gate).

Figure 6:
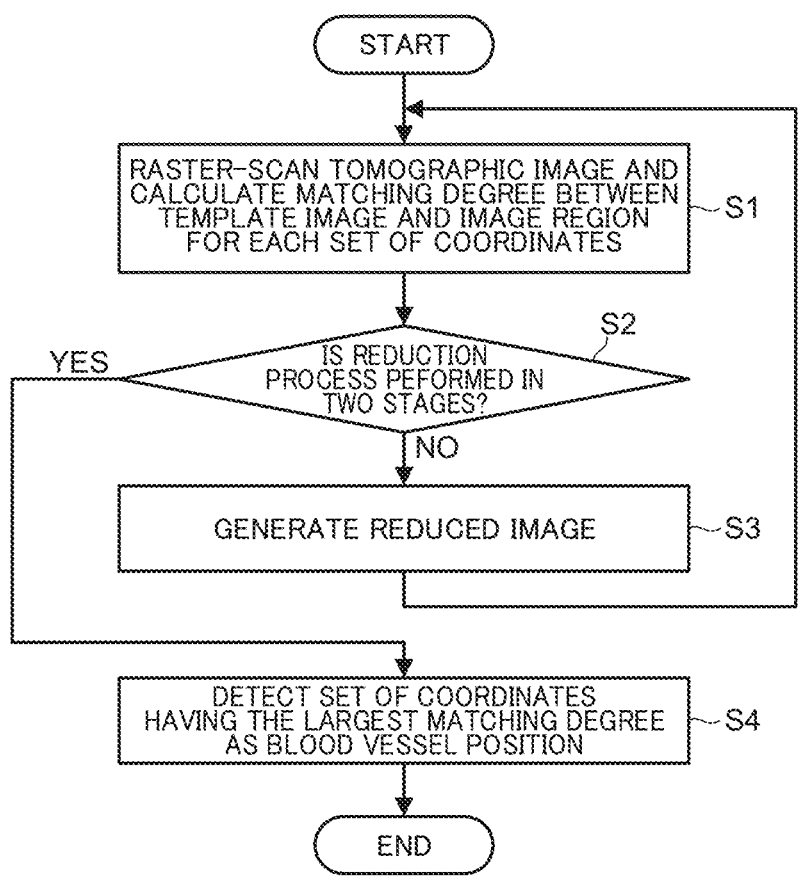
FIG. 6 is a flowchart illustrating an example of processing perforated by a blood vessel detection section.
Figure 7:
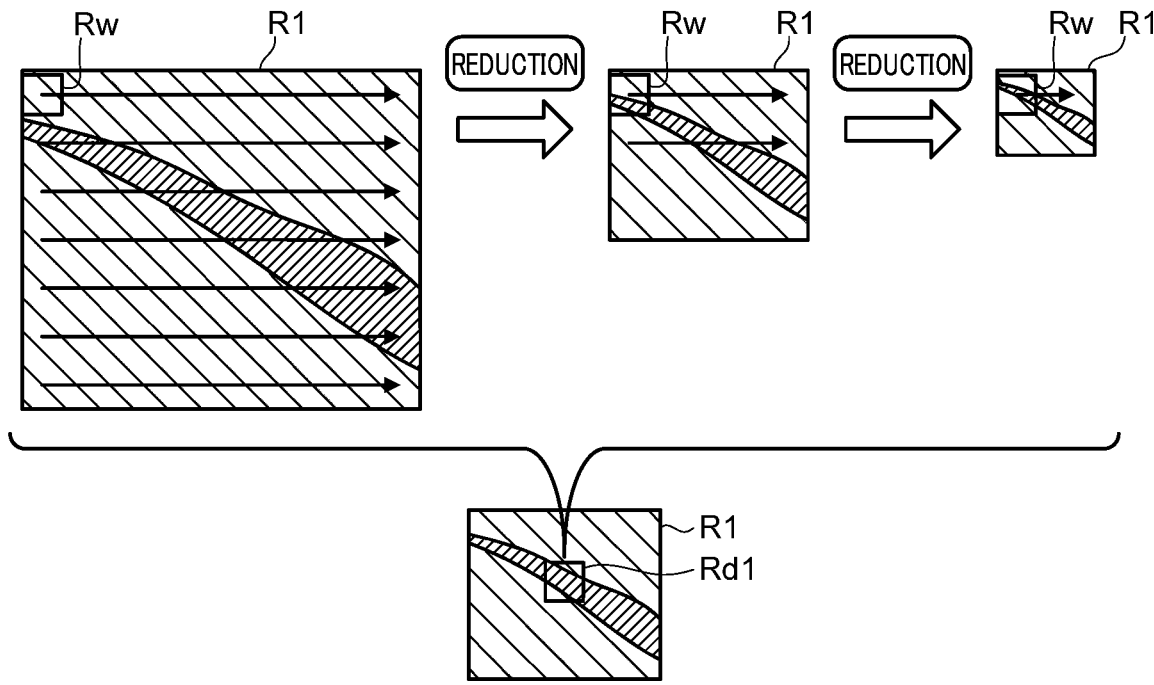
FIG. 7 is a diagram for schematically describing the example of the processing performed by the blood vessel detection section.
Figure 8:
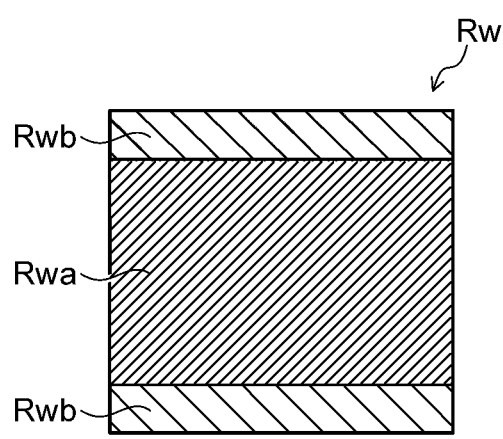
FIG. 8 illustrates an example of a blood vessel template image referenced by the blood vessel detection section.

FIG. 6 is a flowchart illustrating an example of processing performed by blood vessel detection section 12a. FIG. 7 is a diagram for schematically describing the example of processing performed by blood vessel detection section 12a. FIG. 8 illustrates an example of blood-vessel template image Rw referenced by blood vessel detection section 12a.

First, in step S1, blood vessel detection section 12a reads out blood-vessel template image Rw. Then, blood vessel detection section 12a, for example, sequentially sets comparison target image regions (hereinafter, referred to as "comparison target regions") having the same size (for example, 100 pixels×100 pixels) as template image Rw in tomographic image R1 so as to raster-scan an inside of tomographic image R1, and calculates, for each of the comparison target regions, a matching degree (i.e., similarity) with template image Rw. Blood vessel detection section 12a then calculates the matching degree with template image Rw for each set of coordinates in tomographic image R1.

Thus, a region where a blood vessel is imaged clearly in tomographic image R1 is searched.

Note that, as blood-vessel template image Rw referenced by blood vessel detection section 12a, for example, as in FIG. 8, an image is used which has blood vessel region Rwa and tissue regions Rwb, wherein blood vessel region Rwa extends laterally in a center region of the image and tissue regions Rwb are present above and below with blood vessel region Rwa interposed therebetween.

Next, in step S2, blood vessel detection section 12a determines whether a reduction process of the subsequent step S3 has been performed in two stages. Then, in a case where the reduction process in step S3 has been performed in two stages (step S2: YES), the processing proceeds to step S4, in a case where the reduction process in step S3 has not been performed in two stages (step S2: NO), the processing proceeds to step S3.

Next, in step S3, blood vessel detection section 12a reduces tomographic image by a predetermined magnification (e.g., 0.9 times) to generate a reduced image. Then, blood vessel detection section 12a returns to step S1 and similarly performs template matching with respect to the reduced image, using blood-vessel template image Rw, to thereby calculate the matching degree for each set of coordinates of the reduced image. Note that, in this case, a template of the blood vessel applied to original tomographic image R1 is used without changing the size of blood-vessel template image Rw.

Incidentally, a search process using this reduced image is a process considering a case where the size of the blood vessel imaged in tomographic image R1 is different from that of template image Rw.

Next, in step S4, blood vessel detection section 12a selects the set of coordinates having the largest matching degree from among the sets of coordinates of tomographic image R1, the sets of coordinates of the reduced image, and the sets of coordinates of the re-reduced image (tomographic image R1 reduced in two stages).

With such processes, blood vessel detection section 12a searches for a region where the blood vessel is most clearly imaged in tomographic image R1 and of the region (i.e., the center coordinates) as a position of vessel Rd that is a target to be measured in the Doppler mode.

Here, blood-vessel template image Rw used by blood vessel detection section 12a is, for example, as in FIG. 8, typically an image that is similar to a long axis view of a blood vessel, but such template image Rw is also partly similar to a short axis view of a blood vessel. Thus, in the processing by blood vessel detection section 12a, the blood vessel imaged in tomographic image R1 can be detected not only when an image of blood vessel Rd1 imaged in tomographic image R1 is a long axis view, but when the image of blood vessel Rd1 imaged in tomographic image R1 is a short axis view.

A method for detecting a blood vessel by blood vessel detection section 12a is optional, and a discriminator that has been trained by machine learning (e.g., Convolutional Neural Network (CNN)) or the like may be used.

Blood Vessel Image Determination Section 12b

Blood vessel image determination section 12b performs image analysis of tomographic image R1 and determines whether an image of blood vessel Rd1 detected by blood vessel detection section 12a (hereinafter, simply referred to as "blood vessel Rd1") falls under either a short axis view or a long axis view. Blood vessel image determination section 12b determines whether the image of blood vessel Rd1 falls under either the short axis view or long axis view, based on, for example, a distribution of the matching degree between the tomographic image and the template image at the detection position of blood vessel Rd1 and a peripheral position thereof.

FIGS. and 10A to 10C are diagrams for describing an example of determination processing by blood vessel image determination section 12b.

Figure 9:
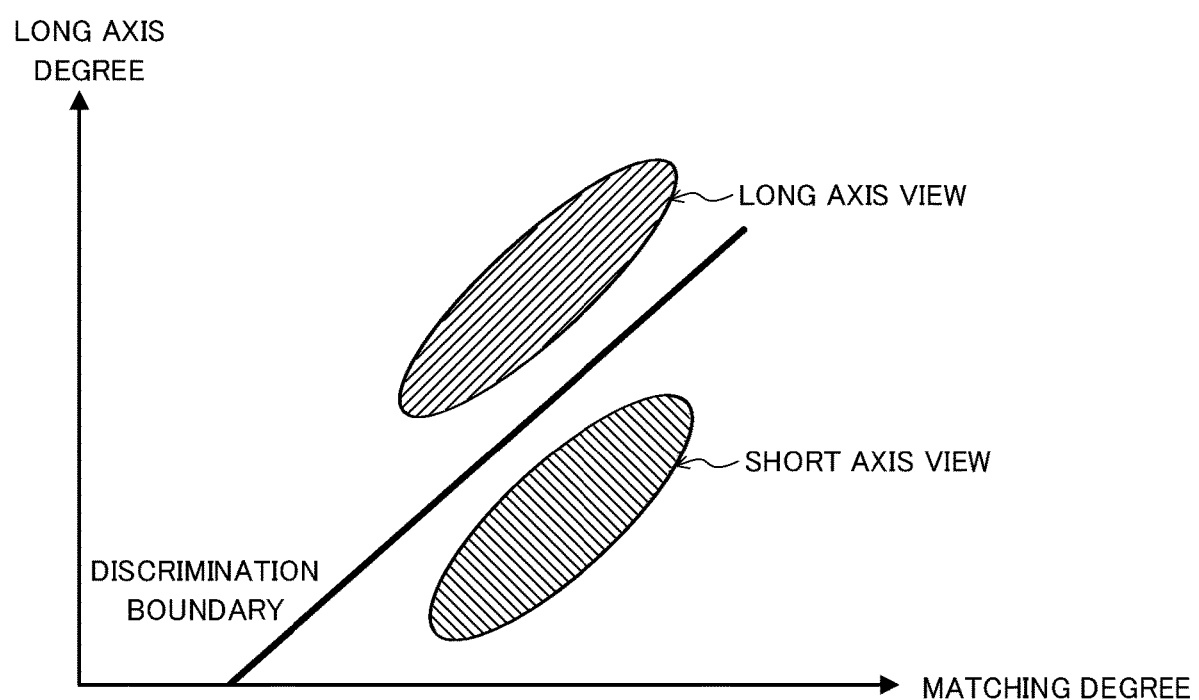
FIG. 9 is a diagram for describing an example of determination processing by a blood vessel determination section.

FIG. 9 illustrates distributions of the matching degree (horizontal axis) and a long axis degree (vertical axis) obtained respectively when the image of blood vessel Rd1 is the short axis view and when the image of blood vessel Rd1 is the long axis view. Incidentally, FIG. 9, also illustrates a discriminant boundary for determining whether the image of blood vessel Rd1 corresponds to either the short axis view or long axis view, which is specified from these distributions.

The "matching degree" illustrated in FIG. 9 refers to a degree of matching at the detection position of blood vessel Rd1. The "long axis degree" illustrated in FIG. 9 refers to a degree of likelihood of being long axis of the image of blood vessel Rd1, and is determined by the distribution of the matching degree between the tomographic image and the template image at the detection position of blood vessel Rd1 and the peripheral position thereof.

Figure 10A:
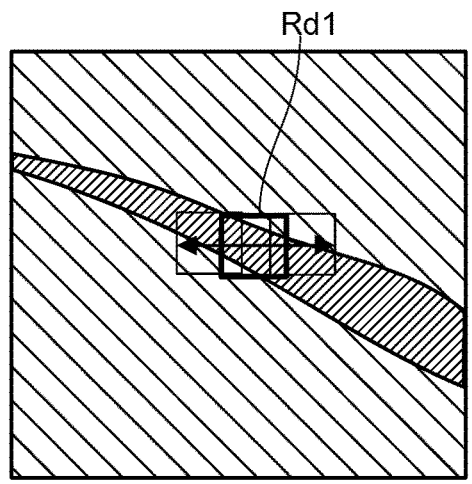
FIG. 10A is another diagram for describing the example of the determination processing by the blood vessel determination section.
Figure 10B:
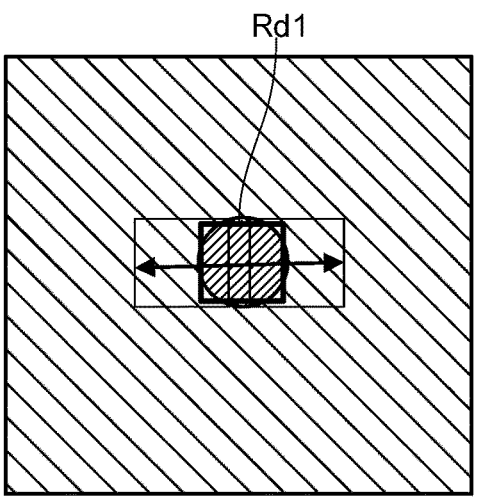
FIG. 10B is still another diagram for describing the example of the determination processing by the blood vessel determination section.

FIGS. 10A and 10B illustrate an example of a method for calculating the long axis degree of blood vessel Rd1 in blood vessel image determination section 12b.

Blood vessel image determination section 12b moves the template image (e.g., template image Rw illustrated in FIG. 8) within predetermined left and right ranges based on, for example, the detection position of blood vessel Rd1 to thereby calculate the matching degree at each of the positions within the predetermined left and right ranges of the detection position of blood vessel Rd1. Then, blood vessel image determination section 12b sets the mean value between the matching degree at the detection position of blood vessel Rd1 and the matching degree at each of the positions within the predetermined left and right ranges as the "long axis degree."

Here, when the image of blood vessel Rd1 is a long axis view, since a high matching degree can be obtained even in the left and right positions of the detection position of blood vessel Rd1, the long axis degree is calculated as a high value (see FIG. 10A). On the other hand, when the image of blood vessel Rd1 is a short axis view, since a matching degree decreases in the left and right positions of the detection position of blood vessel Rd1, the long axis degree is calculated as a low value (see FIG. 10B).

Figure 10C:
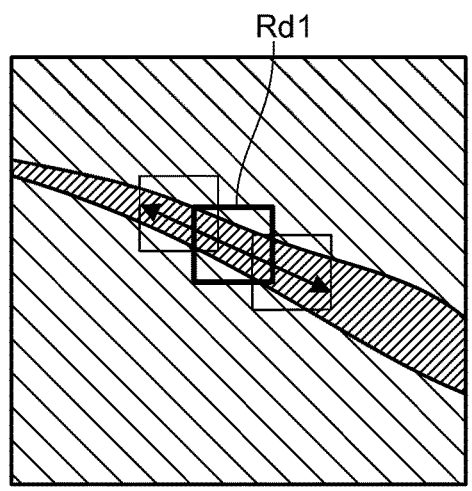
FIG. 10C is yet another diagram for describing the example of the determination processing by the blood vessel determination section.

FIG. 10C illustrates another example of a method for calculating the long axis degree of blood vessel Rd1 in blood vessel image determination section 12b. Blood vessel image determination section 12b, as illustrated in 10C, may estimate an extending direction of blood vessel Rd1 from the distribution of the matching degree at each position around the detection position of blood vessel Rd1 and set the mean value of the matching degrees of each of the positions within the predetermined left and right ranges along the extending direction as the "long axis degree" from the detection position of blood vessel Rd1.

Incidentally, in the above description, the long axis degree has been calculated based on the detection position of blood vessel Rd1 detected by blood vessel detection section 12a, it may be calculated as follows. That is, the long axis degree is obtained in the same manner as described above with respect to the sets of coordinates having the largest matching degrees in, respectively, the original image of tomographic image R1, the reduced image of tomographic image R1, and the re-reduced image of tomographic image R1 (see FIG. 6). Then, the image having the largest long axis degree is selected from among the original image of tomographic image R1, the reduced image of tomographic image R1, and the re-reduced image of tomographic image R1, and the set of coordinates thereof is set as the detection position of a long axis vessel. Determination in FIG. 9 is performed using the long axis degree thus obtained and the matching degree determined in step 4 of the flowchart in FIG. 6. When tomographic image R1 is determined to be a long axis view, the detection position of the above long axis blood vessel is set as the detection position of blood vessel Rd1. On the other hand, when it is determined to be a short axis view, the set of coordinates selected in step 4 is set as the detection position of blood vessel Rd1. In this manner described above, when tomographic image R1 is a long axis view, the coordinates having a high degree of likelihood of being long axis can be determined as the detection position of blood vessel Rd1 by calculating the long axis degrees in, respectively, the original image of tomographic image R1, the reduced image of tomographic image R1, and the re-reduced image of tomographic image R1 and selecting the one having the largest long axis degree.

In addition, the aspect is indicated in which blood vessel image determination section 12b executes again the same process of template matching as blood vessel detection section 12a when calculating the long axis degree, but blood vessel image determination section 12h may calculate the long axis degree, referring to the matching at each position in the tomographic image, which is calculated by blood vessel detection section 12a.

Calculating the long axis degree of blood vessel Rd1 in the manner described above allows determination of whether the image of blood vessel Rd1 is a short axis view or long axis view. In particular, as illustrated in FIG. 9, using the two-axis distribution graph based on the matching degree and the long axis degree enables the determination of whether the image of blood vessel Rd1 is a short axis view or long axis view from the two viewpoints of a local feature of the image at the detection position of blood vessel Rd1 and a broader feature of the image at the periphery of the detection position of blood vessel Rd1; thus, the determination processing will be easier.

Distribution data in FIG. 9 is obtained by, for example, experimentation or simulation in advance, and is stored in a storage of control device 10 (e.g., ROM). Incidentally, distribution data used for performing the determination processing is applicable as long as an evaluation can be performed with two axes of the matching degree and the long axis degree, data may be used on which a normalization process or the like is performed (e.g., a value obtained by dividing the mean value between the matching degree at the detection position of blood vessel Rd1 and the matching degree at each of the positions within the predetermined left and right ranges by the matching degree at the detection position of blood vessel Rd1 is used as the long axis degree).

Sample Gate Setting Section 12c

Sample gate setting section 12c sets the size of a sample gate range gate) when executing the PW Doppler mode, with the detection position of blood vessel Rd1 as a center.

Specifically, sample gate selling section 12c first sets the detection position of blood vessel Rd1 as a center position of the sample gate. Sample gate setting section 12c then sets the size of the sample gate from the vessel size at the detection position of blood vessel Rd1.

Figure 11:
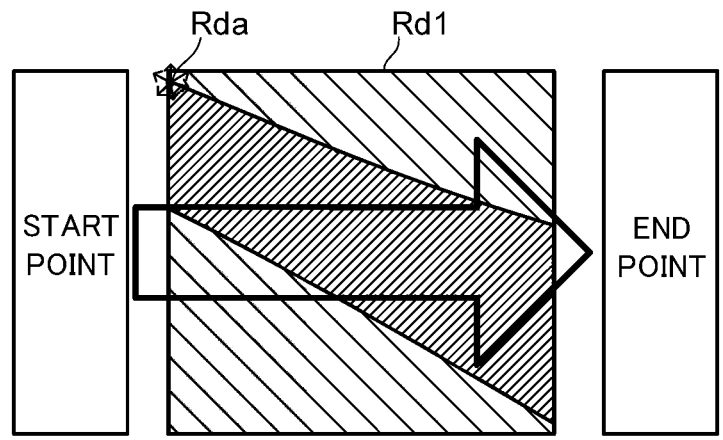
FIG. 11 is a diagram for schematically describing an example of detection processing for a blood vessel size in a sample gate setting section.

FIG. 11 is a diagram for schematically describing an example of detection processing for a blood vessel size in sample gate setting section 12c.

Sample gate setting section 12c, for example, performs a path search in an image region of the detection position of blood vessel Rd1, assuming a path with a strong edge and the edge smoothly continues, as a boundary between the blood vessel and an extravascular tissue. Specifically, sample gate setting section 12c replaces a problem of boundary detection with a problem of searching for a path with which a cost is minimized, and searches for a path with the cost minimized from a left end side (Rda in FIG. 11) of the image range of the detection position of blood vessel Rd1, assuming that directions having a small edge and a non-smooth path are the paths with which the cost increases. Thus, a boundary position between an upper sidewall portion of the blood vessel and the extravascular tissue and a boundary position between a lower sidewall portion of the blood vessel and the extravascular tissue are detected. Sample gate setting section 12c then sets a width between the boundary position of the upper sidewall portion of the blood vessel and the boundary position of the lower sidewall portion of the blood vessel (e.g., the largest value of the blood vessel width calculated at each lateral position) as the size of the sample gate.

In the present embodiment, the aspect is indicated in which sample gate setting section 12c sets the size of the sample gate by using the same method both in cases where the image of blood vessel Rd1 is the short axis view and the image of blood vessel Rd1 is the long axis view. However, sample gate setting section 12c may set the size of the sample gate using different methods between when the image of blood vessel Rd1 is the short axis view and when the image of blood vessel Rd1 is the long axis view. For example, when the image of blood vessel Rd1 is the short axis view, sample gate setting section 12c may set the maximum value of the blood vessel widths calculated at lateral positions as the size of the sample gate whereas, when the image of blood vessel Rd1 is the long axis view, may set the mean value of the blood vessel widths calculated at the lateral positions as the size of the sample gate. This allows the setting of the size of the sample gate to a more appropriate value.

Steering Angle Setting Section 12d

Steering angle setting section 12d sets a steering angle of an ultrasound beam (here, ultrasound beam used when executing the PW Doppler mode) used in measuring a blood now state at the detection position of blood vessel Rd1, based on the determination result by blood vessel image determination section 12b.

Specifically, steering angle setting section 12d sets a steering angle of the ultrasound beam to zero angle when the image of blood vessel Rd1 is a short axis view. On the other hand, steering angle setting section 12d sets a steering angle of the ultrasound beam to an angle corresponding to the extending direction of blood vessel Rd1 in the tomographic image when the image of blood vessel Rd1 is a long axis view.

Note that, when the image of blood vessel Rd1 is the long axis view, steering angle setting section 12d first calculates the extending direction of blood vessel Rd1 and sets the steering angle of the ultrasound beam, referring to the extending direction.

Figure 12:
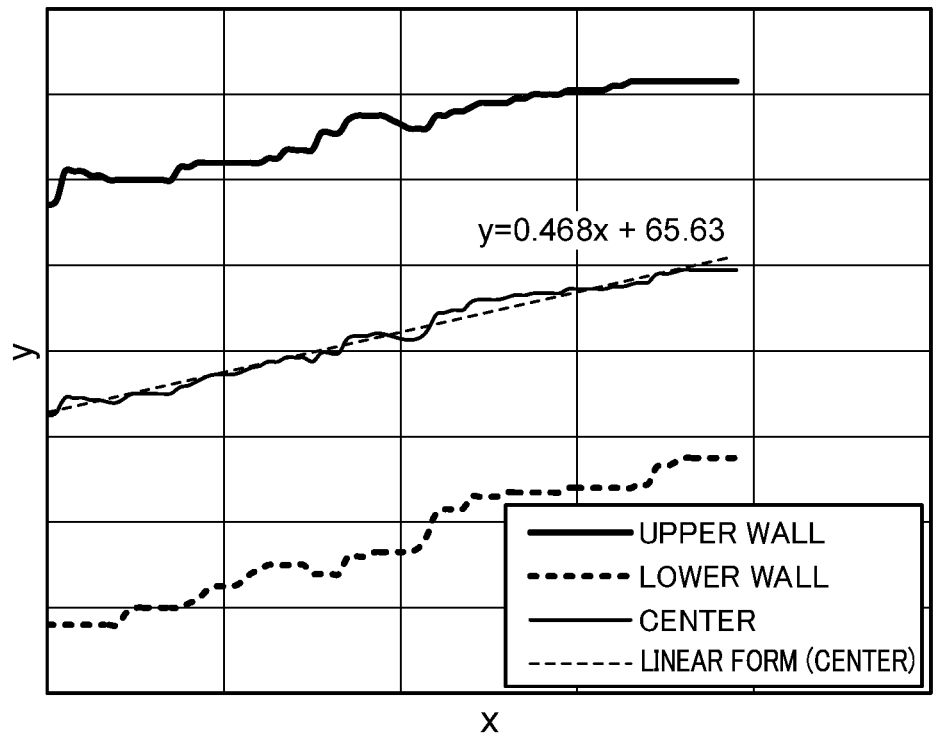
FIG. 12 illustrates an example of calculation processing of an extending direction of a blood vessel in a steering angle setting section.

FIG. 12 illustrates an example of calculation processing of an extending direction of a blood vessel in steering angle setting section 12d. Steering angle setting section 12d calculates, as the extending direction of blood vessel Rd1, the mean value between the extending direction of the boundary of the upper sidewall portion of the blood vessel and the extending direction of the boundary of the lower sidewall portion of the blood vessel, which are specified in the processing by sample gate setting section 12c illustrated in FIG. 11, for example. In FIG. 12, the extending direction of blood vessel Rd1 is calculated as an inclination angle of the XY coordinate system with a scanning direction of tomographic image R1 as an X-axis and a depth direction as a Y-axis.

Figure 13A:
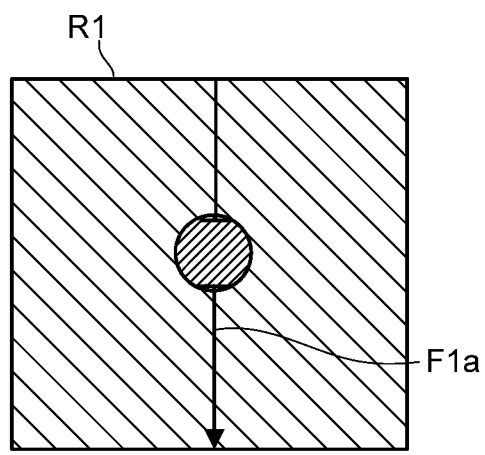
FIG. 13A illustrates an example of steering angle setting processing in the steering angle setting section.
Figure 13B:
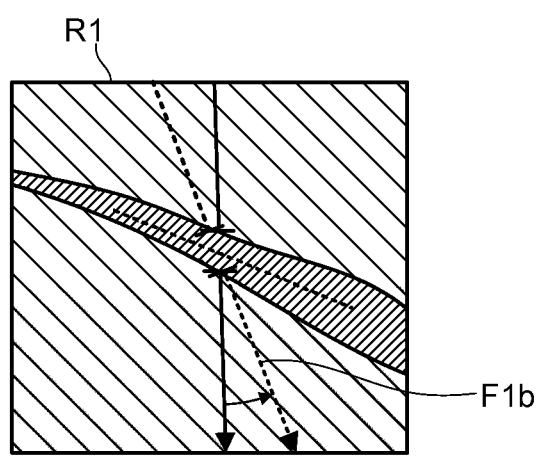
FIG. 13B is another diagram illustrating, the example of the steering angle setting processing in the steering angle setting section.

FIGS. 13A and 13B illustrate an example of steering angle selling processing by steering angle setting section 12d. Incidentally, F1a and F1b in FIGS. 13A and 13B indicate beam directions of ultrasound beams which are set by steering angle setting section 12d.

Generally, when the image of blood vessel Rd1 is the short axis view, a crossing angle between the beam direction of the ultrasound beam mid the blood flow direction does not vary even when the steering angle of the ultrasound beam is changed from zero angle (i.e., tomographic image depth direction) to an angle greater than zero angle. Rather, when the ultrasound beam is transmitted to a blood vessel that is imaged as a short axis view, changing the steering angle from zero angle to an angle greater than zero angle may cause a situation where the ultrasound beam scatters and reflects off the blood vessel wall, and thus, a signal-to-noise (SN) ratio may be reduced.

Thus, steering angle setting section 12d according to the present embodiment sets a steering angle of the ultrasound beam to zero angle when the image of blood vessel Rd1 is a short axis view (see FIG. 13A).

On the other hand, when the image of blood vessel Rd1 is the long axis view, as can be seen from the above Equation 1, the larger the crossing angle between the beam direction of the ultrasound beam and the extending direction (that is, blood flow direction) of blood vessel Rd1, the larger the detection error of the blood flow velocity is.

Thus, steering angle setting section 12d according to the present embodiment, when the image of blood vessel Rd1 is the long axis view, sets the steering angle of the ultrasound beam such that the crossing angle between the beam direction of the ultrasound beam and the extending direction (that is, blood flow direction) of blood vessel Rd1 is as small as possible (sec FIG. 13B). That is, when the image of blood vessel Rd1 is the long axis view, steering angle setting section 12d ideally sets the steering angle of the ultrasound beam such that the beam direction of the ultrasound beam is parallel to the extending direction of blood vessel Rd1.

In practice, however, the steering angle of the ultrasound beam has a limit angle (e.g., 30 degrees); thus, steering angle setting section 12d sets a steering angle of the ultrasound beam to the limit angle in a case where the blood vessel extends horizontally of the tomographic image (i.e., in scanning direction).

In addition, steering angle setting section 12d, after setting the steering angle of the ultrasound beam, sets the angle correction value according to the steering angle. Specifically, when the image of blood vessel Rd1 is the long axis view, steering angle setting section 12d sets "a value corresponding to the crossing angle between the beam direction of the ultrasound beam and the extending direction of blood vessel Rd1" as the angle correction value at the set steering angle. For example, when the crossing angle between the beam direction of the ultrasound beam and the extending direction of blood vessel Rd1 is zero angle, steering angle setting section 12d sets the angle correction value is set to zero angle while setting the angle correction value to "a value obtained by subtracting the value of the limit angle from 90 degrees" when the crossing angle between the beam direction of the ultrasound beam and the extending direction of blood vessel Rd1 is the limit angle of the steering angle. On the other hand, when the image of blood vessel Rd1 is the short axis view, steering angle setting section 12d sets, for example, "0 degrees" as the angle correction value.

Incidentally, information related to: blood vessel detection section 12a; blood vessel image determination section 12b; sample gate setting section 12c; the sample gate position set by steering angle setting section 12d; the determination result of the image blood vessel Rd t whether the long axis or short axis; the size of the sample gate; the steering angle of the ultrasound beam; and the angle correction value is output to display processing section 5 and transmission-reception control section 11 as the transmission and reception conditions of the ultrasound beam when in the PW Doppler mode operation.

Operation of Doppler Parameter Setting Section 12

Figure 14:
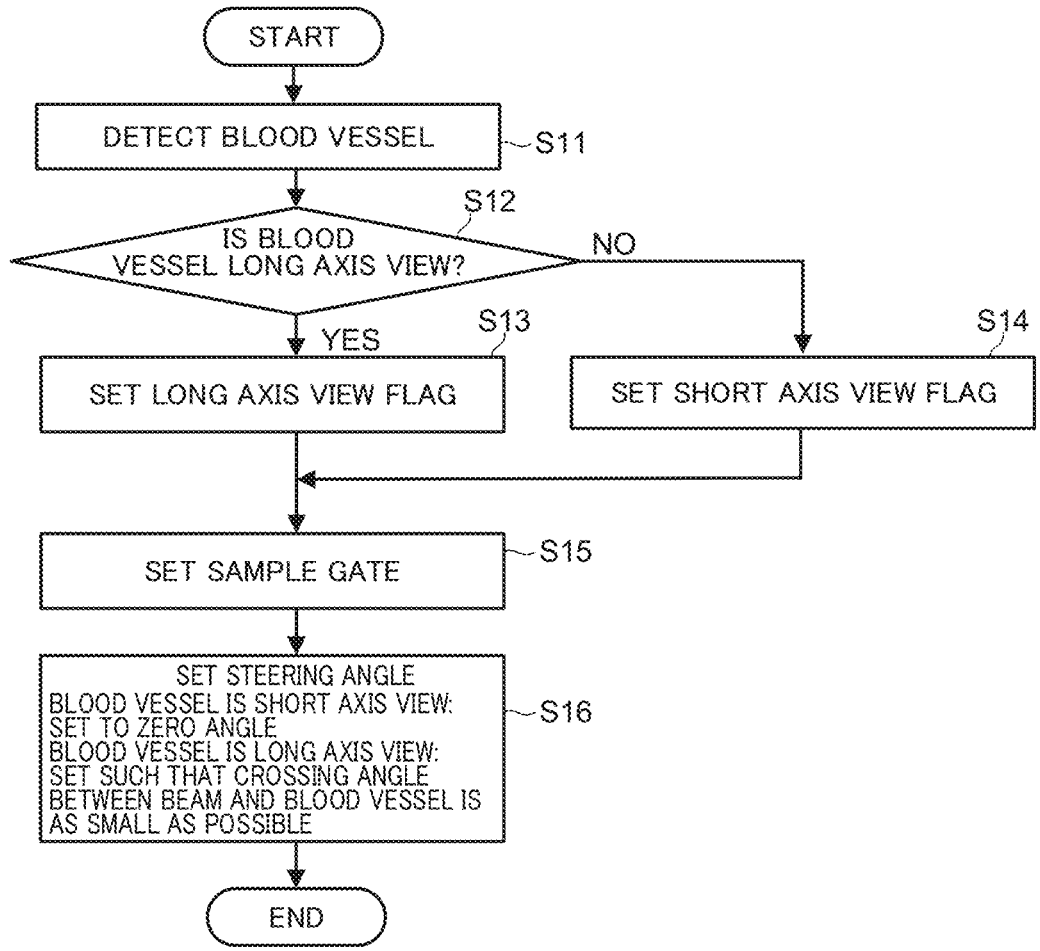
FIG. 14 is a flowchart illustrating an example of an operation of the Doppler parameter setting section.

FIG. 14 is a flowchart illustrating an example of an operation of Doppler parameter setting section 12. The flowchart in FIG. 14 illustrates, for example, a process in which Doppler parameter setting section 12 automatically sets a Doppler parameter when executing the Doppler mode at the timing where an imaging mode is switched from the B mode to the PW Doppler mode.

In step S11, Doppler parameter setting section 12 first obtains tomographic image R1 generated in tomographic image generation section 3 and detects blood vessel Rd1 imaged in tomographic image R1. In this step S11, Doppler parameter setting section 12 detects blood vessel Rd1 imaged in tomographic image R1, for example, by template matching according to the flowchart illustrated in FIG. 6.

In step S12, Doppler parameter setting section 12 determines whether the image of blood vessel Rd1 detected in step S11 is a long axis view. Note that, in this step S12, Doppler parameter setting section 12 determines whether the image of blood vessel Rd1 is a long axis view based on, for example, the matching degree between blood vessel Rd1 and the blood vessel template image and the long axis degree of blood vessel Rd1. Then, when the image of blood vessel Rd1 is the long axis view (S12: YES), Doppler parameter setting section 12 proceeds the processing to step S13, and, after setting a long axis view flag with respect to the image of blood vessel Rd1 (step S13), proceeds the processing to step S15. On the other hand, when the image of blood vessel Rd1 is not the long axis view (S12: NO), Doppler parameter setting section 12 proceeds the processing to step S14, and, after setting a short axis view flag with respect to the image of blood vessel Rd1 (step S14), proceeds the processing to step S15.

In step S15, Doppler parameter setting section 12 sets a sample gate. In this step S15, Doppler parameter setting section 12 detects a width of blood vessel Rd1 and sets the sample gate corresponding to the width of blood vessel Rd1 by using, for example, the method illustrated in FIG. 11.

In step S16, Doppler parameter setting section 12 sets a steering angle. In this step S16, for example, when the image of blood vessel Rd1 is the short axis view, Doppler parameter setting section 12 sets the steering angle to zero angle while, when the image of blood vessel Rd1 is the long axis view, setting the steering angle such that the crossing angle between the ultrasound beam and the extending direction of blood vessel Rd1 is as small as possible.

With the above-described series of processes, Doppler parameter setting section 12 automatically sets the Doppler parameter when executing the Doppler mode.

Effects

As described above, according to ultrasound diagnostic apparatus A according to the present embodiment, a steering angle can be automatically set in an appropriate manner after determining whether the blood vessel imaged in the tomographic image falls under either the long axis view or short axis view. Thus, it is possible to reduce an operation load for a user when executing the Doppler mode and perform measurement of a blood flow state with high reliability.

Variation 1

Figure 15:
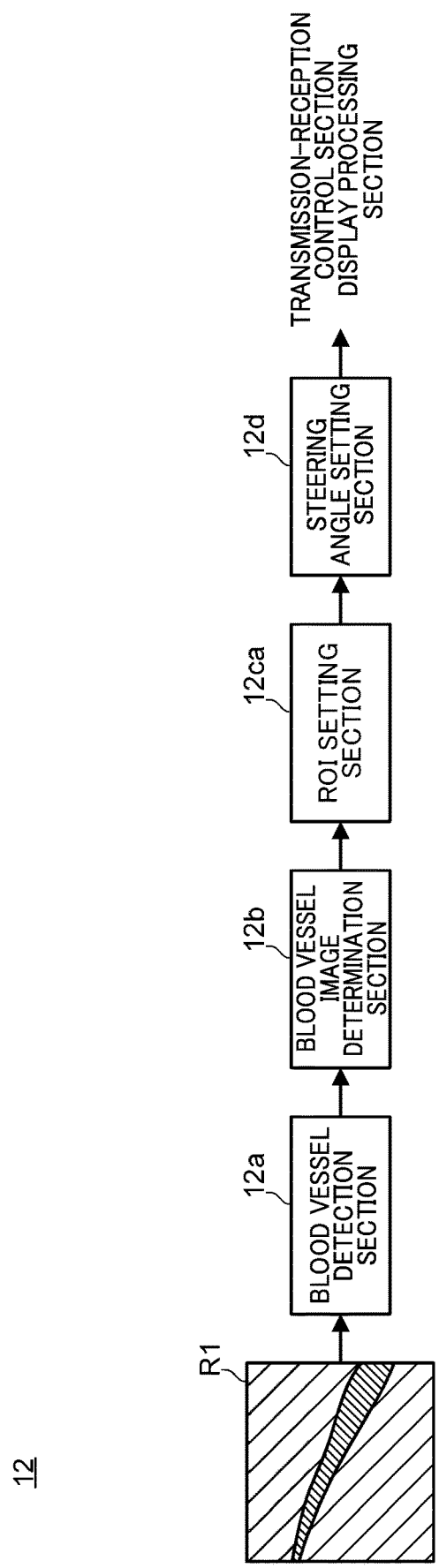
FIG. 15 illustrates a configuration of a Doppler parameter setting section according to Variation 1.

FIG. 15 illustrates a configuration of Doppler parameter setting section 12 according to Variation 1. Doppler parameter setting section 12 according to Variation 1 is a setting section that functions when executing the color Doppler mode, and is different from Doppler parameter setting section 12 illustrated in FIG. 5 in that ROI setting section 12ca is provided instead of sample gate setting section 12c.

ROI setting section 12ca sets a ROI to be a measurement target when executing the color Doppler mode, with the detection position of blood vessel Rd1 detected by blood vessel detection section 12a as a center.

Figure 16A:
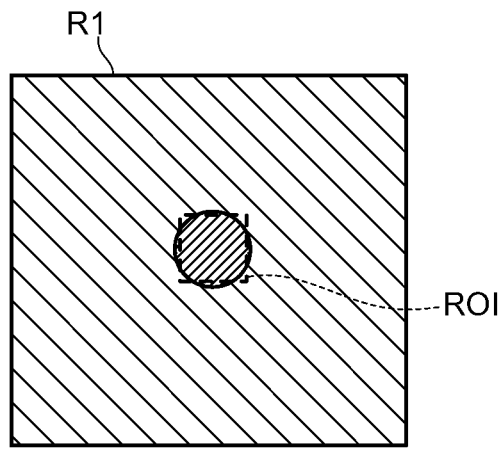
FIG. 16A illustrates an example of a ROI sat by a ROI setting section according to Variation 1.
Figure 16B:
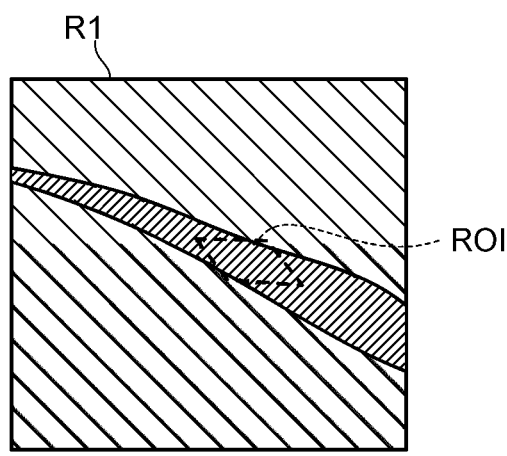
FIG. 16B is another diagram illustrating the example of the ROI set by the 1101 setting section according to Variation 1.

FIGS. 16A and 16B illustrate an example of a ROI set by ROI setting section 12ca. FIG. 16A illustrates the ROI (dotted line region in FIG. 16A) set by ROI setting section 12ca when blood vessel Rd1 is the short axis view, and FIG. 16B illustrates the ROT (dotted line region in FIG. 16B) set by ROI setting section 12ca when blood vessel Rd1 is the long axis view. Incidentally, in FIG. 16B, the ROI is in the region of a parallelogram because a steering angle is set in an ultrasound beam when blood vessel Rd1 is the long axis view.

First, ROI setting section 12ca detects the blood vessel size at the detection position of blood vessel Rd1 by using, for example, the method illustrated in FIG. 11. Next, ROI setting section 12ca sets the blood vessel size at the detection position of blood vessel Rd1 as a range in a depth direction of the ROI. ROI setting section 12ca then sets a range in a scanning direction of the ROI.

Here, regarding the range in the scanning direction of the ROI, ROI setting section 12ca may change the setting method depending on whether the image of blood vessel Rd1 is either a short axis view or a long axis view. Specifically, ROI setting section 12ca may set a preset range as the range in the scanning direction of the ROI when the image of blood vessel Rd1 is the long axis view whereas the same size as the range in the depth direction of the ROI may be set as the range in the scanning direction of the ROI when the image of blood vessel Rd1 is the short axis view. This is because blood vessel Rd1 is observed in a generally circular shape when the image of blood vessel Rd1 is the short axis view.

Note that, in FIGS. 16A and 16B, a case is illustrated in which the blood vessel size of blood vessel Rd1 is set as the range in the depth direction of the ROI, but a range larger than the blood vessel size of blood vessel Rd1 may be set by adding a predetermined offset value. In addition, the range of the ROI may be set to a predefined size around the detection position of blood vessel Rd1.

As described above, according to ultrasound diagnostic apparatus A according to Variation 1, even when executing the color Doppler mode, the Doppler parameters (e.g., ROI and steering angle) can be appropriately set.

Here, a description has been given of a the configuration of Doppler parameter setting section 12 in a case where ultrasound diagnostic apparatus A includes the function of executing the color Doppler mode; however, by using the same configuration, a configuration of Doppler parameter setting section 12 in a case where ultrasound diagnostic apparatus A includes the function of executing the power Doppler mode can be achieved.

Variation 2

Display processing section 5 may display, redisplay image Tall, a determination result by blood vessel image determination section 12b.

Figure 17:
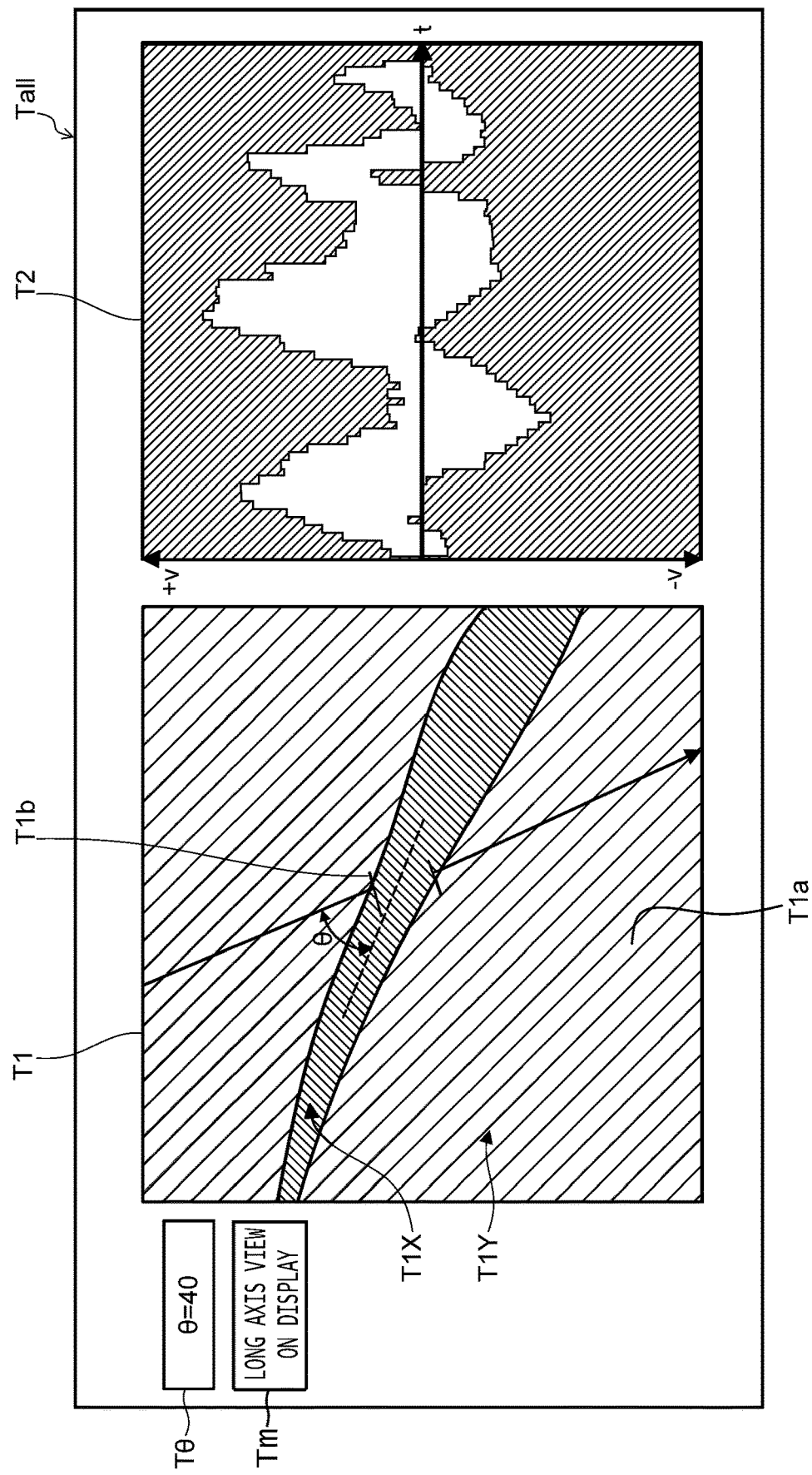
FIG. 17 illustrates an example of a display image displayed by a display processing section according to Variation 2.

FIG. 17 illustrates an example of display image Tall displayed by display processing section 5 according to Variation 2. Display processing section 5 according to Variation 2 is configured to obtain a determination result from Doppler parameter setting section 12 as to whether blood vessel Rd1 is either a long axis view or short axis view and to display content Tm corresponding to the determination result in display image Tall.

Thus, displaying the determination result by blood vessel image determination section 12b in display image Tall allows the user to easily recognize whether the blood vessel currently being a measurement target is either a long axis view or short axis view.

As described above, according to ultrasound diagnostic apparatus A according to Variation 2, it is possible to further improve the convenience during ultrasonography of the blood flow state.

Variation 3

Display processing section 5 may display guide image T1g indicating the detection position and the extending direction of blood vessel Rd1 by superimposing guide image T1g on tomographic image R1 (here, tomographic image displayed in the T1 region in FIG. 4).

Generally, ultrasound diagnostic apparatus A is used for diagnosing body tissue by inserting a puncture needle into a body of a patient that is the subject to collect tissue or body fluid, and/or for performing a treatment using the puncture needle. In these diagnostics or treatments, a user (e.g., doctor) performs puncture while checking a position of a puncture needle and a position of a part to be punctured (target) by viewing a tomographic image obtained by ultrasound diagnostic apparatus A.

Considering such a utilization mode of ultrasound diagnostic apparatus A, display processing section. 5 according to Variation 3 displays, in guide image T1g, the detection position and extending direction of blood vessel Rd1 to assist the user in a insertion operation of the puncture needle.

Figure 18A:
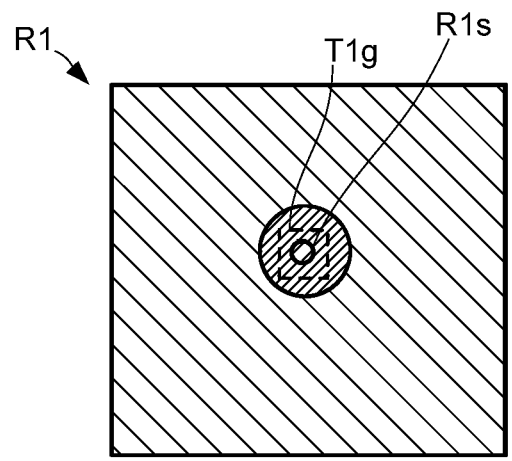
FIG. 18A illustrates an example of a guide image displayed by a display processing section according to Variation 3.
Figure 18B:
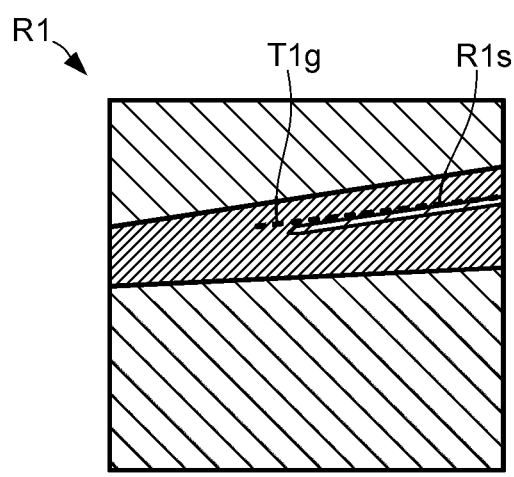
FIG. 18B is another diagram illustrating the example of the guide image displayed by the display processing section according to Variation 3.

FIGS. 18A and 18B illustrate an example of guide image T1g displayed by display processing section 5 according to Variation 3. FIG. 18A illustrates guide image T1g to be displayed when blood vessel Rd1 detected in tomographic image R1 is the short axis view whereas FIG. 18B illustrates guide image T1g to be displayed when blood vessel Rd1 detected in tomographic image R1 is the long axis view. Incidentally, both of FIGS. 18A and 18B represent tomographic images in a state where puncture needle R1s is inserted into the blood vessel.

Here, display processing section 5 according to Variation 3 changes the image type of guide image T1g depending on whether the image of blood vessel Rd1 falls under either a short axis view or long axis view, as illustrated in FIGS. 18A and 18B. Specifically, display processing section 5, for example, when the image of blood vessel Rd1 is the short axis view, displays guide image T1g having a shape that allows a center position of a lateral cross-section of blood vessel Rd1 to be identified (rectangular in FIG. 18A). On the other hand, display processing section 5, for example, when the image of blood vessel Rd1 is the long axis view, displays guide image T1g having a shape that allows an extending direction of a center of the vessel of a longitudinal cross-section of blood vessel Rd1 to be identified (line shape in the FIG. 18B).

Incidentally, display processing section 5 determines the image type of guide image T1g based on, for example, the position of blood vessel Rd1 output from Doppler parameter setting section 12, the determination result of either the long axis or short axis of the image of blood vessel Rd1, and the information on the extending direction of blood vessel Rd1, determines the display position of guide image T1g, and thereby displays guide image T1g as illustrated in FIGS. 18A and 18B.

Thus, the user can grasp the insertion direction of puncture needle R1s by visually recognizing guide image T1g.

As described above, according to ultrasound diagnostic apparatus A according to Variation 3, it is possible to further improve the convenience during ultrasonography of the blood flow state.

Variation 4

Ultrasound diagnostic apparatus A (e.g., control device 10) may include a first data processing section (not illustrated) that stores the determination result by blood vessel image determination section 12b in a memory in association with tomographic image R1.

The first data processing section, for example, from Doppler parameter setting section 12, obtains a determination result as to whether blood vessel Rd1 is either a long axis view or short axis view. Then the first data processing section stores the determination result, in association with tomographic image R1, in an external storage device (e.g., cine memory that temporarily stores a plurality of frame images obtained in the previous few minutes so as to be reproducible in moving images), for example. In this case, the tomographic image with which the first data processing section associates the determination result by blood vessel image determination section 12b may be tomographic image R1 as raw data generated by tomographic image generation section 3 or a display image in which tomographic image R1 generated by display processing section 5 is embedded.

This allows the user to search for a desired tomographic image with a search flag from the external storage device and to browse the desired tomographic image after the end of the ultrasonography.

As described above, according to ultrasound diagnostic apparatus A according to Variation 4, it is possible to further improve the convenience during ultrasonography of the blood flow state.

Variation 5

Ultrasound diagnostic apparatus A (e.g., control device 10) may include a second data processing section (not illustrated) that monitors a temporal variation in the determination results by blood vessel image determination section 12b, and when the determination result by blood vessel image determination section 12b varies, compares the blood vessel sizes of blood vessel Rd1 related to the short axis view and long axis view each detected before and after the variation, and thereby notifies the user of a comparison result.

As described above, ultrasound diagnostic apparatus A measures the amount of blood flow in the long axis view after observing the blood vessel at the same location in each of the short axis view and long axis view. At this time, an inspector checks whether a diameter of the blood vessel observed or measured in the short axis view is the same as the diameter of the blood vessel measured in the long axis view, and thereby determines whether the ultrasound beam passes through a center of the blood vessel. Thus, it will be convenient that whether the diameter of the blood vessel in the short axis view and the diameter of the blood vessel in the long axis view are the same is easily determinable.

From this point of view, the second data processing section obtains various kinds of data from Doppler parameter setting section 12 (here, data related to the blood vessel size and the determination result by blood vessel image determination section 12b) and detects that blood vessel Rd1 imaged in tomographic image R1 has changed from the short axis view to the long axis view, and/or blood vessel Rd1 imaged in tomographic image R1 has changed from the long axis view to the short axis view, as the user moves and rotates ultrasound probe 200. Then, when blood vessel Rd1 imaged in tomographic image R1 has changed from the short axis view to the long axis view or when blood vessel Rd1 imaged at tomographic image R1 has changed from the long axis view to the short axis view, the second data processing section compares the size of blood vessel Rd1 detected at the time of the short axis view and the size of blood vessel Rd1 detected at the time of the long axis view with each other, and thereby notifies, as a result of the comparison, the likelihood of the coincidence between the size of the short axis view and the size of the long axis view size, which are detected before and after the variation.

This allows the user to easily recognize whether the ultrasound beam passes through a center of the blood vessel, that is, an appropriate long axis view of the blood vessel at the same location is obtained when the user moves or rotates ultrasound probe 200.

Figure 19:
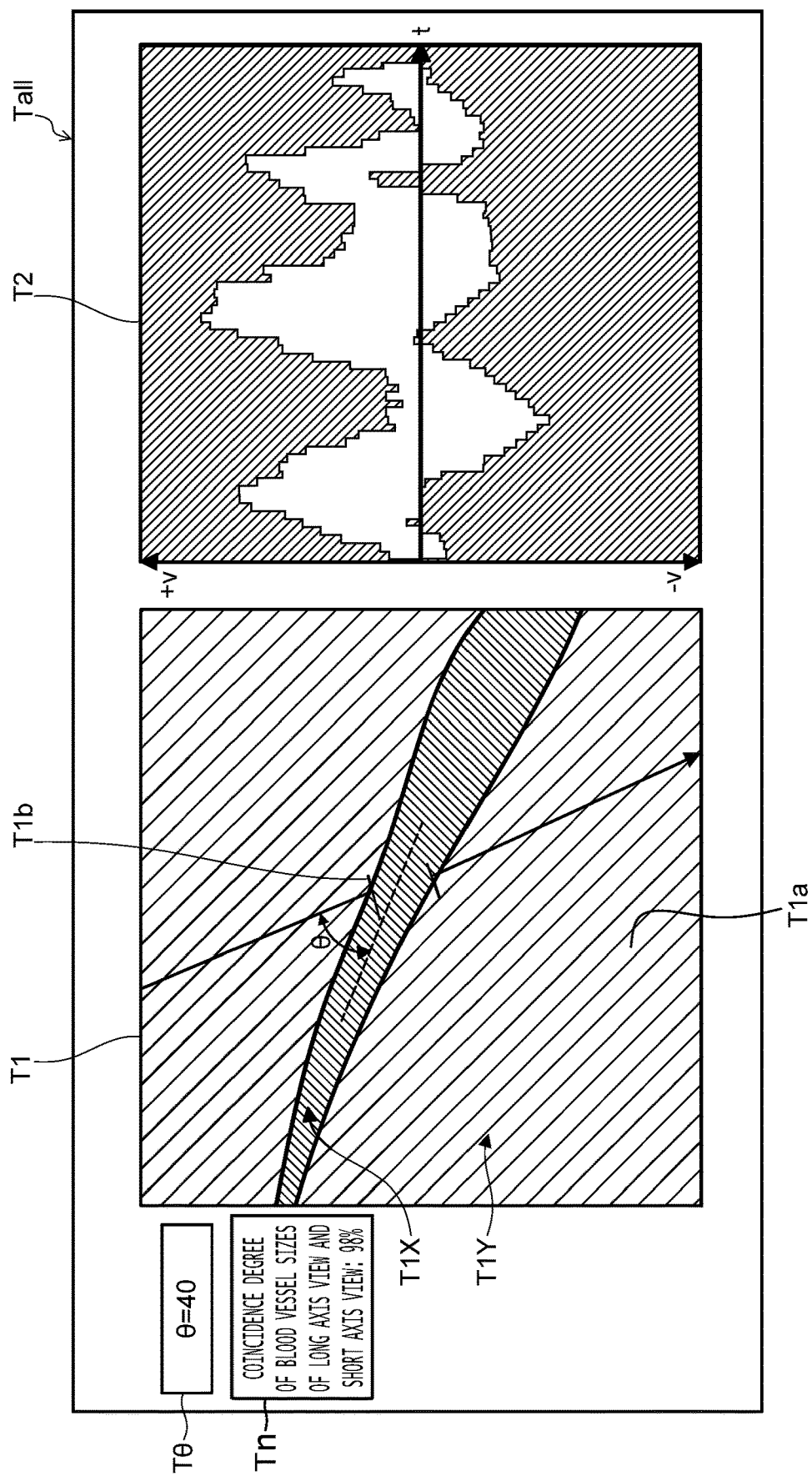
FIG. 19 illustrates an example of an aspect in which a comparison result is notified by the second data processing section according to Variation 5.

FIG. 19 illustrates an example of an aspect in which a comparison result is notified by the second data processing section. In FIG. 19, the aspect is indicated in which second data processing section displays coincidence degree Tn of the sizes of the blood vessel associated with the short axis view and long axis view, respectively, in display image Tall generated by display processing section 5.

As described above, according to ultrasound diagnostic apparatus A according to Variation 5, it is possible to further improve the convenience during ultrasonography of the blood flow state.

Variation 6

Ultrasound diagnostic apparatus A (e.g., control device 10) may include a third data processing section (not illustrated) that automatically sets a measurement item related to conditions of blood vessel Rd1. An example of the measurement item set by the third data processing section include, for example, a measurement item for measuring a narrowing rate of blood vessel Rd1 from the image of blood vessel Rd1.

Figure 20:
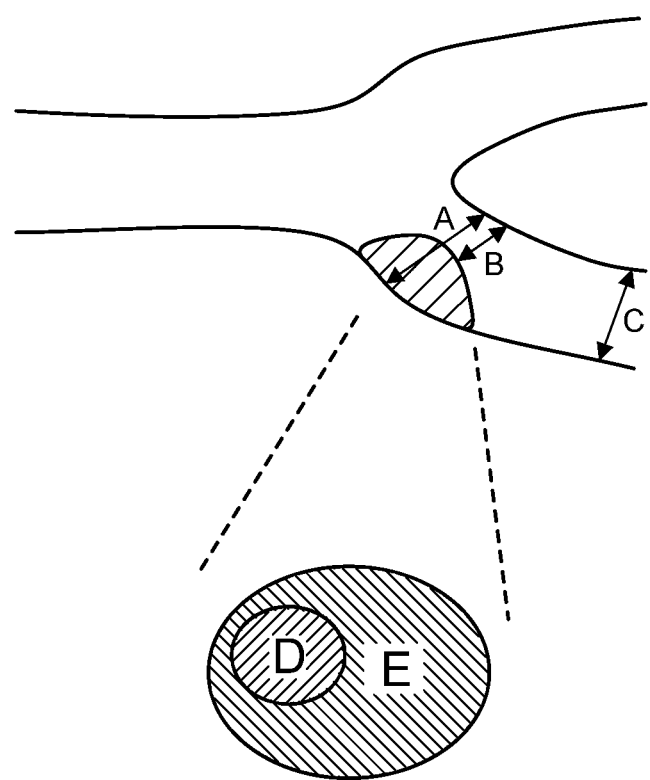
FIG. 20 is a diagram for describing a common measurement method of a narrowing rate of a blood vessel.

FIG. 20 is a diagram for describing a common measurement method of a narrowing rate of a blood vessel. An upper diagram of FIG. 20 illustrates a state where the blood vessel of the long axis view is observed in the tomographic image, whereas the lower diagram of FIG. 20 illustrates a state where the blood vessel of the short axis view is observed in the tomographic image.

Generally, as a measurement method of the narrowing rate of a blood vessel, for example, a North American Symptomatic Endarterectomy Trial (NASCET) method, an European Carotid Surgery Trial (ECST) method, and an area stenosis method are known. The NASCET method expresses the narrowing rate of a blood vessel with the following expression: (vessel width C−vessel width B/vessel width C)×100%, illustrated in the upper diagram of FIG. 20. The ECST method expresses the narrowing rate of a blood vessel with the following expression: (vessel width A−vessel width B/vessel width B)×100%. The area stenosis method expresses the narrowing rate of a blood vessel with the following expression: (blood vessel region area E−blood vessel region area D/blood vessel region area E)×100%, illustrated in the lower diagram of FIG. 20. The NASCET method and ECST method are for expressing the narrowing rate of a blood vessel when the image of a blood vessel is a long axis view whereas the area stenosis method is for expressing the narrowing rate of a blood vessel whets the image of a blood vessel is a short axis view.

Thus, considering that the expression method is different depending on whether the image of the blood vessel is either the short axis view or long axis view in expressing the narrowing rate of a blood vessel, the third data processing section sets the measurement item (e.g., items for inputting vessel width A and vessel width B) such that the narrowing rate of a blood vessel can be expressed by using, for example, the NASCET method when the image of blood vessel Rd1 detected in tomographic image R1 is the long axis view (upper diagram of FIG. 20), while setting the measurement item (e.g., items for inputting blood vessel region area D and blood vessel region area E) such that the narrowing rate of a blood vessel can be expressed by using, for example, the area stenosis method when the image of blood vessel Rd1 detected in tomographic image R1 is the short axis view (lower diagram of FIG. 20).

Note that, measurement of blood vessel width A, blood vessel width B and blood vessel width C illustrated in the upper diagram of FIG. 20, and measurement of blood vessel region area D and blood vessel region area E illustrated in the lower diagram of FIG. 20 are preferably automatically performed by an image recognition process (e.g., publicly known template matching). However, the measurement itself may be performed by visual input of the user.

As described above, according to ultrasound diagnostic apparatus A according to Variation 6, it is possible to further improve the convenience during ultrasonography of the blood flow state.

Variation 7

Ultrasound diagnostic apparatus A (e.g., control device 10) may include B steering setting section 12x that sets a steering angle of an ultrasound beam when executing the B-mode (also referred to as B steer) based on the image information on tomographic image R1.

Figure 21:
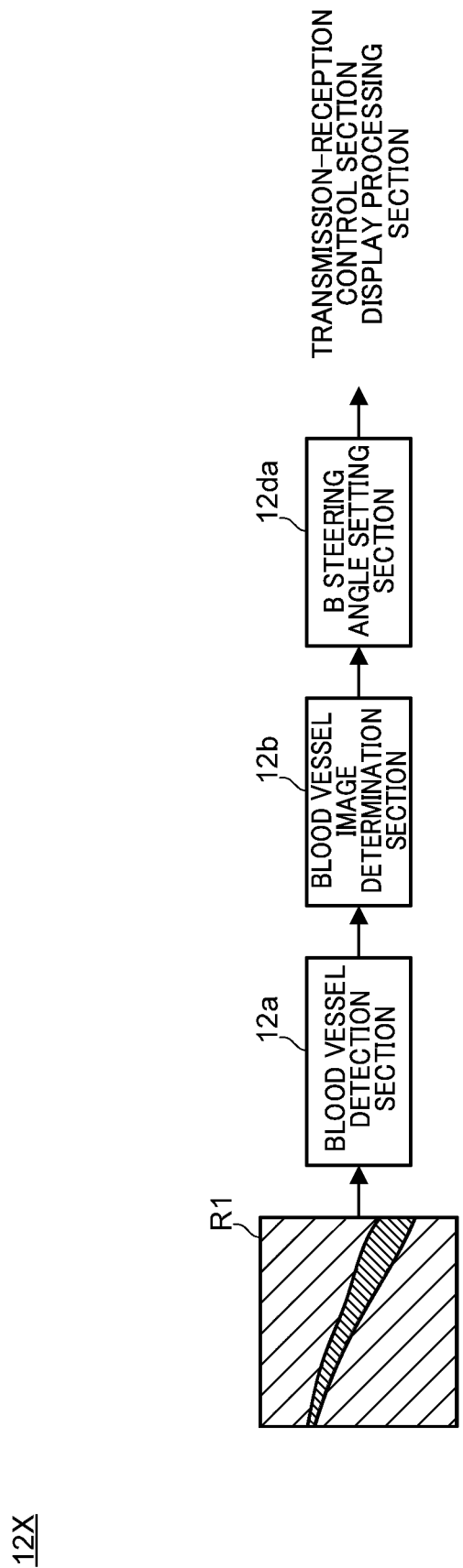
FIG. 21 illustrates an example of a configuration of a B steering setting section according to Variation 7.

FIG. 21 illustrates an example of a configuration of B steering selling section 12x.

B steering setting section 12x includes, for example, blood vessel detection section 12a, blood vessel image determination section 12h, and B steering angle setting section 12da. Here, the configurations of blood vessel detection section 12a and blood vessel image determination section 12b included in B steering angle setting section 12da are the same as those of blood vessel detection section 12a and blood vessel image determination section 12b included in Doppler parameter setting section 12. B steering angle setting section 12da sets a steering angle in executing the B-mode, by using the same method as steering angle setting section 12d included in Doppler parameter setting section 12, based on the determination result by blood vessel image determination section 12b.

Figure 22A:
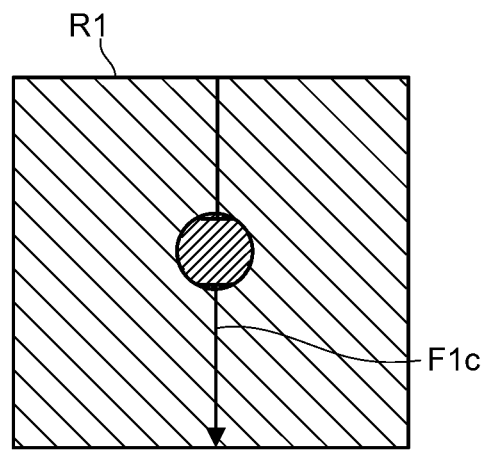
FIG. 22A illustrates an example of B steering setting processing by the B steering setting section according to Variation 7.
Figure 22B:
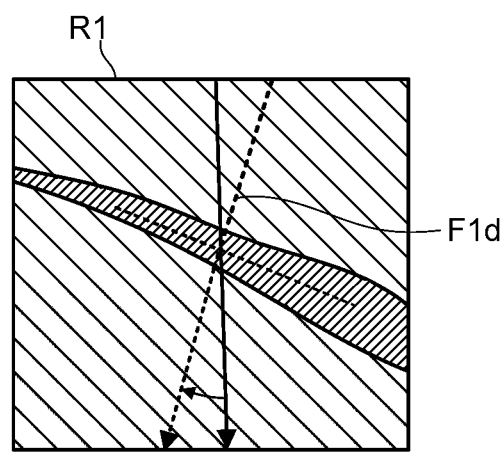
FIG. 22B is another diagram illustrating, the example of the B steering setting processing by the B steering setting section according to Variation 7.

FIGS. 22A and 22B illustrate an example of steering angle setting processing by B steering angle setting section 12da. Incidentally, F1c and F1d in FIGS. 22A and 22B indicate beam directions of ultrasound beams which are set by B steering angle setting section 12da.

When it is desired to clearly draw a blood vessel wall or the like in the tomographic image, the beam direction of the ultrasound beam in executing the B mode is preferably brought close to 90 degrees with respect to the extending direction of the blood vessel. However, considering a scattered reflection or the like off the blood vessel wall, in the case of setting a steering angle of the B-steer, as in the case of setting the steering angle in executing the Doppler mode, setting contents of the steering angle needs to be changed based on whether blood vessel R1d imaged in tomographic image R1 is either a long axis view or short axis view.

From this point of view, B steering setting section 12x according to Variation 7 determines whether blood vessel Rd1 is either a long axis view or short axis view after detecting blood vessel Rd1 imaged in the tomographic image. Then, when blood vessel Rd1 is the short axis view, B steering setting section 12x sets a steering angle of the B-steer to zero angle (see FIG. 22A). On the other hand, when blood vessel Rd1 is the long axis view, B steering setting section 12x detects the extending direction of blood vessel Rd1 and sets a steering angle of the B-steer such that the beam direction of the ultrasound beam is as close as possible to 90 degrees with respect to the extending direction of the blood vessel (see FIG. 22B).

As described above, according to ultrasound diagnostic apparatus A according to Variation 7, the steering angle in executing the B-mode can be appropriately set, and conditions of the blood vessel can be more clearly drawn in the tomographic image.

Although embodiments of the present invention have been described and illustrated in detail, the disclosed embodiments are made for purpose of illustration and example only and not limitation. The scope of the present invention should be interpreted by terms of the appended claims.

INDUSTRIAL APPLICABILITY

According to the ultrasound diagnostic apparatus according to the present disclosure, it is possible to reduce an operation load for a user when executing the Doppler mode and perform measurement of a blood flow state with high reliability.

What is claimed is:

1. An ultrasound diagnostic apparatus for generating a tomographic image of a subject by transmitting and receiving an ultrasound, the ultrasound diagnostic apparatus comprising:
a hardware processor that:
detects a blood vessel imaged in the tomographic image;
determines whether a view of the blood vessel which has been detected is either a short axis view or a long axis view by an image analysis of the tomographic image;
sets a steering angle of an ultrasound beam used in measuring conditions of the detected blood vessel or a blood flow velocity in the detected blood vessel,
the steering angle of the ultrasound beam being set to zero relative to a depth direction when the view of the detected blood vessel is the short-axis view, and
the steering angle of the ultrasound beam being set so that a crossing angle, between a beam direction of the ultrasound beam and an extending direction of the detected blood vessel, is at a predetermined value when the view of the detected blood vessel is the long-axis view;
automatically selectively drives transducers of an ultrasound probe to generate the ultrasound beam at the steering angle; and
automatically sets a measurement item to be measured related to determining a condition of the detected blood vessel, the measurement item being a parameter to be measured, and changes the parameter to be measured for determining the condition of the detected blood vessel, depending on whether the view of the detected blood vessel falls under either the short axis view or the long axis view.

2. The ultrasound diagnostic apparatus according to claim 1, wherein
the hardware processor determines whether the view of the detected blood vessel falls under either the short axis view or the long axis view, based on a distribution of a matching degree of template matching using a blood vessel template image at a position where the blood vessel has been detected and a periphery of the position.

3. The ultrasound diagnostic apparatus according to claim 2, wherein the hardware processor determines whether the view of the blood vessel which has been detected is either the short axis view or the long axis view by calculating the matching degree of template matching using the blood vessel template image that is moves at positions within predetermined left and right ranges based on the position where the blood vessel has been detected.

4. The ultrasound diagnostic apparatus according to claim 2, wherein
the hardware processor calculates a long axis degree of the image of the detected blood vessel at the position where the blood vessel has been detected and the periphery of the position, and determines whether the view of the detected blood vessel falls under either the short axis view or the long axis view, based on an evaluation of the long axis degree and the matching degree at the position where the detected blood vessel has been detected.

5. The ultrasound diagnostic apparatus according to claim 1, wherein
the hardware processor generates a display image including the tomographic image and displays, in the display image, a determination result of whether the view of the blood vessel falls under either the short axis view or the long axis view.

6. The ultrasound diagnostic apparatus according to claim 1, wherein
the hardware generates a display image including the tomographic image, and displays while superimposing, on the tomographic image, a guide image indicating a position of the detected blood vessel, and changes an image type of the guide image depending on whether the view of the detected blood vessel falls under either the short axis view or the long axis view.

7. The ultrasound diagnostic apparatus according to claim 6, wherein the guide image is a short axis guide image having a shape that identifies a center position of a lateral cross-section of the detected blood vessel when the view of the detected blood vessel is the short axis view and the guide image is a long axis guide image having a shape that indicates an extending direction of a center of a longitudinal cross-section of the detected blood vessel when the view of the detected blood vessel is the long axis view.

8. The ultrasound diagnostic apparatus according to claim 1, wherein
the hardware processor stores, in a memory, a determination result of whether the view of the detected blood vessel falls under either the short axis view or the long axis view in association with the tomographic image.

9. The ultrasound diagnostic apparatus according to claim 1, wherein the hardware processor:
monitors a temporal variation in determination results of whether the view of the detected blood vessel falls under either the short axis view or the long axis view,
compares, when the determination result varies, blood vessel sizes of the blood vessel related to the short axis view and long axis view each detected before and after the temporal variation, and
notifies a user of a comparison result.

10. The ultrasound diagnostic apparatus according to claim 1, wherein
the measurement item is for measuring a narrowing rate of the blood vessel from the detected blood vessel.

11. The ultrasound diagnostic apparatus according to claim 1, wherein
the ultrasound beam is an ultrasound beam used in generating a Doppler image related to at least one of a B mode image, a color Doppler mode, a power Doppler mode, and/or PW Doppler mode.

12. The ultrasound diagnostic apparatus according to claim 1, further comprising the ultrasound probe that transmits the ultrasound beam toward the subject and receives an ultrasound echo of the ultrasound beam from an inside of the subject.

13. The ultrasound diagnostic apparatus according to claim 1, wherein
the measurement item to be measured is a blood vessel width when the view of the detected blood vessel is the long-axis view and the measurement item to be measured is a blood vessel region area when the view of the detected blood vessel is the short-axis view.

14. The ultrasound diagnostic apparatus according to claim 13, wherein
the measurement item is for measuring a narrowing rate of the blood vessel from the detected blood vessel.

15. A method of controlling an ultrasound diagnostic apparatus for generating a tomographic image of a subject by transmitting and receiving an ultrasound, the method comprising:
detecting a blood vessel imaged in the tomographic image;
determining whether a view of the blood vessel which has been detected falls under either a short axis view or a long axis view by an image analysis of the tomographic image; and
setting a steering angle of an ultrasound beam used in measuring conditions of the detected blood vessel or a blood flow velocity in the detected blood vessel,
the steering angle of the ultrasound beam being set to zero relative to a depth direction when the view of the detected blood vessel is the short-axis view, and
the steering angle of the ultrasound beam being set so that a crossing angle, between a beam direction of the ultrasound beam and an extending direction of the detected blood vessel, is at a predetermined value when the view of the detected blood vessel is the long-axis view;
automatically selectively driving transducers of an ultrasound probe to generate the ultrasound beam at the steering angle; and
automatically setting a measurement item to be measured related to determining a condition of the detected blood vessel, the measurement item being a parameter to be measured, and changing the parameter to be measured for determining the condition of the detected blood vessel, depending on whether the view of the detected blood vessel falls under either the short axis view or the long axis view.

16. A non-transitory computer-readable recording medium storing therein a computer readable program for controlling an ultrasound diagnostic apparatus for generating a tomographic image of a subject by transmitting and receiving an ultrasound, the program causing a computer to perform processing comprising:
detecting a blood vessel imaged in the tomographic image;
determining whether a view of the blood vessel which has been detected falls under either a short axis view or a long axis view by an image analysis of the tomographic image; and
setting a steering angle of an ultrasound beam used in measuring conditions of the detected blood vessel or a blood flow velocity in the detected blood vessel,
the steering angle of the ultrasound beam being set to zero relative to a depth direction when the view of the detected blood vessel is the short-axis view, and
the steering angle of the ultrasound beam being set so that a crossing angle, between a beam direction of the ultrasound beam and an extending direction of the detected blood vessel, is at a predetermined value when the view of the detected blood vessel is the long-axis view; and
automatically selectively driving transducers of an ultrasound probe to generate the ultrasound beam at the steering angle; and
automatically setting a measurement item to be measured related to determining a condition of the detected blood vessel, the measurement item being a parameter to be measured, and changing the parameter to be measured for determining the condition of the detected blood vessel, depending on whether the view of the detected blood vessel falls under either the short axis view or the long axis view.

* * * * *